United States Patent [19]
Deisher et al.

[11] Patent Number: 5,989,866
[45] Date of Patent: Nov. 23, 1999

[54] FGF HOMOLOGS

[75] Inventors: Theresa A. Deisher; Darrell C. Conklin; Fenella Raymond; Thomas R. Bukowski, all of Seattle; Susan D. Holderman, Kirkland; Birgit Hansen, Seattle; Paul O. Sheppard, Redmond, all of Wash.

[73] Assignee: ZymoGenetics, Inc., Seattle, Wash.

[21] Appl. No.: 08/951,822

[22] Filed: Oct. 16, 1997

Related U.S. Application Data

[60] Provisional application No. 60/028,646, Oct. 16, 1996.
[51] Int. Cl.[6] ............................ C12N 15/18; C12N 15/63; C12N 1/21; C12N 5/00
[52] U.S. Cl. .................... 435/69.4; 435/243; 435/320.1; 435/325; 536/23.51; 935/13
[58] Field of Search ............................ 435/69.4, 320.1, 435/70.1, 325, 243; 536/23.51; 935/13

[56] References Cited

U.S. PATENT DOCUMENTS

| | | |
|---|---|---|
| 5,439,818 | 8/1995 | Fiddes et al. . |
| 5,514,566 | 5/1996 | Fiddes et al. . |
| 5,604,293 | 2/1997 | Fiddes et al. . |

OTHER PUBLICATIONS

Ohbayashi et al. J. Biol. Chem. 273(29):18161–18164, 1998.
Hu et al. Mol. Cell. Biol. 18(10):6063–6074, 1998.
Ayala et al. Modern Genetics, Benjamin/Cummings Pub. Co., CA, pp. 44,46 and Glossary, 1984.
Long et al., *Cell Regulation 2*: 1081–1095, 1991.
Lifeseq™ Clone Information Results, Incyte Pharmaceuticals Inc., 1995.
Goldfarb, *Cell Growth and Differentiation 1*: 439–445, 1990.
Crossley et al., *Cell 84*: 127–136, 1996.

*Primary Examiner*—John Ulm
*Assistant Examiner*—Christine Saoud
*Attorney, Agent, or Firm*—Deborah A. Sawislak

[57] ABSTRACT

The present invention relates to polynucleotide and polypeptide molecules for zFGF-5 a novel member of the FGF family. The polypeptides, and polynucleotides encoding them, are proliferative for muscle cells and may be used for remodelling cardiac tissue and improving cardiac function. The present invention also includes antibodies to the zFGF-5 polypeptides.

15 Claims, 3 Drawing Sheets

```
FHF-1       ----------MAAAIASSLIRQKRQARESNS-DRVSASKRRSSPSKDG-R 38
FGF-10      ------------------------------------------------- 
FHF-4       ----------MAAAIASGLIRQKRQAREQHW-DRPSASRRRSSPSKN--R 37
FHF-2       ----------MAAAIASSLIRQKRQARER---EKSNACKCVSSPSKG--K 35
FHF-3       -----------MAALASSLIRQKREVREPGG-SRPVSAQRRVCP-RGT-K 36
FGF4_HUMAN  ----------MS-GPGTAAVALLPAVLLALL-APWAGRGGAAAPTAPN-G 37
FGF6_HUMAN  MALGQKLFITMSRGAGRLQGTLWALVFLGIL-VGMVVP--SPAGTRAN-N 46
FGF2_HUMAN  ------------------------------------------------- 
FGF1_HUMAN  ------------------------------------------------- 
KGF-2       -----------MWKWILTHCASAFPHLPGCCC-CCFLLLFLVSSVPVTC-Q 38
FGF7_HUMAN  -----------MHKWILTWILPTLLYR-S-----CFHIICLVGTISLAC-N 33
ZGI_HUZFGF  -----------MY-SAPSACTCLCLHFLLLCF-QVQ-------VLVAEE-N 30
FGF8_HUMAN  -----------MG-SPRSALSCLLLHLLVLCL-QAQEGPGRGPALGREL-A 37
FGF5_HUMAN  -----------MSLSFLLLLFFSHLILSAWAHGEKRLAPKGQPGPAATDRN 40
FGF9_HUMAN  ------------MAPLGEVGNYFGVQDAVPFGNVPVLP--VDSPVLLS-D 35
FGF3_HUMAN  ---------------MGLIWLLLLSLLEP-------G-----WPAAGPGA 23

FHF-1       SLCERHV---LGVFSKVRFCSGR----------KRPVRRRPEPQLKGIVT 75
FGF-10      -----------------------------------MASKEPQLKGIVT 13
FHF-4       GLCNGNL---VDIFSKVRIFGLK----------KRRLRRQ-DPQLKGIVT 73
FHF-2       TSCDKNK---LNVFSRVKLFGSK----------KRRRRRP-EPQLKGIVT 71
FHF-3       SLCQKQL---LILLSKVRLCGGRP---------ARPDRGP-EPQLKGIVT 73
FGF4_HUMAN  TLEAELERR-WESLVALSLARLPVAAQPKE-AAVQSGAGDYLLG-IKRLR 84
FGF6_HUMAN  TLLDS--RG-WGTLLSRSRAGL---AG--E-IAGVNWESGYLVG-IKRQR 86
FGF2_HUMAN  ----------MAAGSITTLPALPE---------DGGSGAFPPGHFKDPK 30
FGF1_HUMAN  ----------MAEGEITTFTALTE---------KFN---LPPGNYKKPK 27
KGF-2       ALGQDMVSP-EATNSSSSSFSSPSSAG------RHVRSYNHLQG-DVRWR 80
FGF7_HUMAN  DMTPEQM----ATNVNCS---SPE---------RHTRSYDYMEGGDIRVR 67
ZGI_HUZFGF  VDFRID-----------VEK-------------QTRARDDVSRKQLRLY 55
FGF8_HUMAN  SLFRAGR---EPQGVSQQHVRE-----------QSLVTDQLSRRLIRTY 72
FGF5_HUMAN  PIGSSSRQSSSSAMSSSSASSSPAASLGSQGSGLEQSSFQWSPS-GRRTG 89
FGF9_HUMAN  HLGQS------E--AGGLPRGP-----------AVTDLDHLKG-ILRRR 64
FGF3_HUMAN  RLRRD--------------AGG-----------RGGVYEHLGG-APRRR 46

FHF-1       RLFSQQ--GYFLQMHPDGTIDGTKDENSDYTLFNLIPVGLR-VVAIQGVK 122
FGF-10      RLFSQQ--GYFLQMHPDGTIDGTKDENSDYTLFNLIPVGLR-VVAIQGVK 60
FHF-4       RLYCRQ--GYYLQMHPDGALDGTKDDSTNSTLFNLIPVGLR-VVAIQGVK 120
FHF-2       KLYSRQ--GYHLQLQADGTIDGTKDEDSTYTLFNLIPVGLR-VVAIQGVQ 118
FHF-3       KLFCRQ--GFYLQANPDGSIQGTPEDTSSFTHFNLIPVGLR-VVTIQSAK 120
FGF4_HUMAN  RLYCNVGIGFHLQALPDGRIGGAHADT-RDSLLELSPVERG-VVSIFGVA 132
FGF6_HUMAN  RLYCNVGIGFHLQVLPDGRISGTHEEN-PYSLLEISTVERG-VVSLFGVR 134
FGF2_HUMAN  RLYCKNG-GFFLRIHPDGRVDGVREKSDPHIKLQLQAEERG-VVSIKGVC 78
FGF1_HUMAN  LLYCSNG-GHFLRILPDGTVDGTRDRSDQHIQLQLSAESVG-EVYIKSTE 75
KGF-2       KLFSFT--KYFLKIEKNGKVSGTKKENCPYSILEITSVEIG-VVAVKAIN 127
FGF7_HUMAN  RLFCRT--QWYLRIDKRGKVKGTQEMKNNYNIMEIRTVAVG-IVAIKGVE 114
ZGI_HUZFGF  QLYSRTS-GKHIQVLG-RRISARGEDGDKYAQLLVETDTFGSQVRIKGKE 103
FGF8_HUMAN  QLYSRTS-GKHVQVLANKRINAMAEDGDPFAKLIVETDTFGSRVRVRGAE 121
FGF5_HUMAN  SLYCRVGIGFHLQIYPDGKVNGSHEAN-MLSVLEIFAVSQG-IVGIRGVF 137
FGF9_HUMAN  QLYCRT--GFHLEIFPNGTIQGTRKDHSRFGILEFISIAVG-LVSIRGVD 111
FGF3_HUMAN  KLYCAT--KYHLQLHPSGRVNGSLENS-AYSILEITAVEVG-IVAIRGLF 92
              *:.       .:      :.        :..     *  .
```

Fig. 1

```
FHF-1       ASLYVAMNGEGYLYSSDV-FTPECKFKESVFENYYVIYSSTLYRQQESG- 170
FGF-10      ASLYVAMNGEGYLYSSDV-FTPECKFKESVFENYYVIYSSTLYRQQESG- 108
FHF-4       TGLYIAMNGEGYLYPSEL-FTPECKFKESVFENYYVIYSSMLYRQQESG- 168
FHF-2       TKLYLAMNSEGYLYTSEL-FTPECKFKESVFENYYVTYSSMIYRQQQSG- 166
FHF-3       LGHYMAMNAEGLLYSSPH-FTAECRFKECVFENYYVLYASALYRQRRSG- 168
FGF4_HUMAN  SRFFVAMSSKGKLYGSPF-FTDECTFKEILLPNNYNAYESYKYPG----- 176
FGF6_HUMAN  SALFVAMNSKGRLYATPS-FQEECKFRETLLPNNYNAYESDLYQG----- 178
FGF2_HUMAN  ANRYLAMKEDGRLLASKC-VTDECFFFERLESNNYNTYRSRKYTS----- 122
FGF1_HUMAN  TGQYLAMDTDGLLYGSQT-PNEECLFLERLEENHYNTYISKKHAEK--N- 121
KGF-2       SNYYLAMNKKGKLYGSKE-FNNDCKLKERIEENGYNTYASFNWQHN--G- 173
FGF7_HUMAN  SEFYLAMNKEGKLYAKKE-CNEDCNFKELILENHYNTYASAKWTHN--G- 160
ZGI_HUZFGF  TEFYLCMNRKGKLVGKPDGTSKECVFIEKVLENNYTALMSAKYSG----- 148
FGF8_HUMAN  TGLYICMNKKGKLIAKSNGKGKDCVFTEIVLENNYTALQNAKYEG----- 166
FGF5_HUMAN  SNKFLAMSKKGKLHASAK-FTDDCKFRERFQENSYNTYASAIHRTEKTG- 185
FGF9_HUMAN  SGLYLGMNEKGELYGSEK-LTQECVFREQFEENWYNTYSSNLYKHVDTG- 159
FGF3_HUMAN  SGRYLAMNKRGRLYASEH-YSAECEFVERIHELGYNTYASRLYRTVSSTP 141
            :: *.  *  *    .  :*:*.  *    .

FHF-1       ---------RAWFLGLNKEGQIMKG--NRVKKTKPSSHFVPKPIEVCMYR 209
FGF-10      ---------RAWFLGLNKEGQIMKG--NRVEKTKPSSHFVPKPIEVCMYR 147
FHF-4       ---------RAWFLGLNKEGQAMKG--NRVKKTKPAAHFLPKPLEVAMYR 207
FHF-2       ---------RGWYLGLNKEGEIMKG--NHVKKNKPAAHFLPKPLKVAMYK 205
FHF-3       ---------RAWYLGLDKEGQVMKG--NRVKKTKAAAHFLPKLLEVAMYQ 207
FGF4_HUMAN  -----------MFIALSKNGKTKKG--NRVSPTMKVTHFLPRL------ 206
FGF6_HUMAN  -----------TYIALSKYGRVKRG--SKVSPIMTVTHFLPRI------ 208
FGF2_HUMAN  -----------WYVALKRTGQYKLG--SKTGPGQKAILFLPMSAKS---- 155
FGF1_HUMAN  -----------WFVGLKKNGSCKRG--PRTHYGQKAILFLPLPVSSD--- 155
KGF-2       ---------RQMYVALNGKGAPRRG--QKTRRKNTSAHFLPMVVHS---- 208
FGF7_HUMAN  ---------GEMFVALNQKGIPVRG--KKTKKEQKTAHFLPMAIT----- 194
ZGI_HUZFGF  -----------WYVGFTKKGRPRKG--PKTRENQQDVHFMKRYPKGQPEL 185
FGF8_HUMAN  -----------WYMAFTRKGRPRKG--SKTRQHQREVHFMKRLPRGHHTT 203
FGF5_HUMAN  ---------REWYVALNKRGKAKRGCSPRVKPQHISTHFLPRFKQSEQ-P 225
FGF9_HUMAN  ---------RRYYVALNKDGTPREG--TRTKRHQKFTHFLPRPVDPDKVP 198
FGF3_HUMAN  GARRQPSAERLWYVSVNGKGRPRRG--FKTRRTQKSSLFLPRVLDHRDHE 189
            :: ..    *    *   :.      *:

FHF-1       EPSLHEIGEKQ----GRS--RKSSGTPTMNGGKVVNQDST---------- 243
FGF-10      EPSLHEIGENK----GVQ--GKFWTPP----------------------- 168
FHF-4       EPSLHDVGETVPKP-GVTPSKSTSASAIMNGGKPVNKSKTT--------- 247
FHF-2       EPSLHDLTEFSRSG-SGTPTKSRSVSGVLNGGKSMSHNEST--------- 245
FHF-3       EPSLHSVPEAS-------P--SSPPAP----------------------- 225
FGF4_HUMAN  --------------------------------------------------
FGF6_HUMAN  --------------------------------------------------
FGF2_HUMAN  --------------------------------------------------
FGF1_HUMAN  --------------------------------------------------
KGF-2       --------------------------------------------------
FGF7_HUMAN  --------------------------------------------------
ZGI_HUZFGF  QKPFKYTTVTK-----RSRR--IRPTHPA--------------------- 207
FGF8_HUMAN  EQSLRFEFLNYPPF-TRSLRGSQRTWAPEPR------------------- 233
FGF5_HUMAN  ELSFTVTVPEKKNP-PSPIKSKIPLSAPRKNTNSVKYRLKFRFG------ 268
FGF9_HUMAN  ELYKDILSQS---------------------------------------- 208
FGF3_HUMAN  MVRQLQSGLPRPPGKGVQPRRRRQKQSPDNLEPSHVQASRLGSQLEASAH 239
```

Fig. 2

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | 1.00 | 0.39 | 0.43 | 0.29 | 0.46 | 0.33 | 0.36 | 0.38 | 0.37 | 0.41 | 0.39 | 0.40 | 0.42 | 0.40 | 0.35 | 0.38 |
| 2 | | 1.00 | 0.38 | 0.34 | 0.41 | 0.35 | 0.38 | 0.33 | 0.38 | 0.44 | 0.39 | 0.37 | 0.37 | 0.39 | 0.35 | 0.60 |
| 3 | | | 1.00 | 0.31 | 0.42 | 0.34 | 0.33 | 0.36 | 0.34 | 0.38 | 0.35 | 0.37 | 0.41 | 0.46 | 0.35 | 0.35 |
| 4 | | | | 1.00 | 0.34 | 0.53 | 0.26 | 0.24 | 0.26 | 0.31 | 0.28 | 0.30 | 0.30 | 0.31 | 0.28 | 0.32 |
| 5 | | | | | 1.00 | 0.35 | 0.39 | 0.43 | 0.39 | 0.39 | 0.43 | 0.42 | 0.44 | 0.43 | 0.40 | 0.43 |
| 6 | | | | | | 1.00 | 0.33 | 0.31 | 0.33 | 0.31 | 0.32 | 0.34 | 0.34 | 0.32 | 0.36 | 0.36 |
| 7 | | | | | | | 1.00 | 0.34 | 0.98 | 0.33 | 0.76 | 0.81 | 0.34 | 0.37 | 0.67 | 0.42 |
| 8 | | | | | | | | 1.00 | 0.34 | 0.54 | 0.34 | 0.37 | 0.36 | 0.36 | 0.34 | 0.38 |
| 9 | | | | | | | | | 1.00 | 0.33 | 0.66 | 0.72 | 0.34 | 0.37 | 0.62 | 0.42 |
| 10 | | | | | | | | | | 1.00 | 0.32 | 0.35 | 0.40 | 0.37 | 0.32 | 0.43 |
| 11 | | | | | | | | | | | 1.00 | 0.68 | 0.36 | 0.38 | 0.58 | 0.41 |
| 12 | | | | | | | | | | | | 1.00 | 0.36 | 0.33 | 0.62 | 0.42 |
| 13 | | | | | | | | | | | | | 1.00 | 0.47 | 0.34 | 0.32 |
| 14 | | | | | | | | | | | | | | 1.00 | 0.30 | 0.31 |
| 15 | | | | | | | | | | | | | | | 1.00 | 0.38 |
| 16 | | | | | | | | | | | | | | | | 1.00 |

Fig. 3

FGF HOMOLOGS

REFERENCE TO RELATED APPLICATIONS

This application is related to Provisional Application 60/028,646, filed on Oct. 16, 1996. Under 35 U.S.C. § 119(e) (1), this application claims benefit of said Provisional Application.

BACKGROUND OF THE INVENTION

The fibroblast growth factor (FGF) family consists of at least nine distinct members (Basilico et al., *Adv. Cancer Res.* 59:115–165, 1992 and Fernig et al., *Prog. Growth Factor Res.* 5(4):353–377, 1994) which generally act as mitogens for a broad spectrum of cell types. For example, basic FGF (also known as FGF-2) is mitogenic in vitro for endothelial cells, vascular smooth muscle cells, fibroblasts, and generally for cells of mesoderm or neuroectoderm origin, including cardiac and skeletal myocytes (Gospodarowicz et al., *J. Cell. Biol.* 70:395–405, 1976; Gospodarowicz et al., *J. Cell. Biol.* 89:568–578, 1981 and Kardami, *J. Mol. Cell. Biochem.* 92:124–134, 1990). In vivo, bFGF has been shown to play a role in avian cardiac development (Sugi et al., *Dev. Biol.* 168:567–574, 1995 and Mima et al., *Proc. Nat'l. Acad. Sci.* 92:467–471, 1995), and to induce coronary collateral development in dogs (Lazarous et al., *Circulation* 94:1074–1082, 1996). In addition, non-mitogenic activities have been demonstrated for various members of the FGF family. Non-proliferative activities associated with acidic and/or basic FGF include: increased endothelial release of tissue plasminogen activator, stimulation of extracellular matrix synthesis, chemotaxis for endothelial cells, induced expression of fetal contractile genes in cardiomyocytes (Parker et al., *J. Clin. Invest.* 85:507–514, 1990), and enhanced pituitary hormonal responsiveness (Baird et al., *J. Cellular Physiol.* 5:101–106, 1987.)

Several members of the FGF family do not have a signal sequence (aFGF, bFGF and possibly FGF-9) and thus would not be expected to be secreted. In addition, several of the FGF family members have the ability to migrate to the cell nucleus (Friesel et al., *FASEB* 9:919–925, 1995). All the members of the FGF family bind heparin based on structural similarities. Structural homology crosses species, suggesting a conservation of their structure/function relationship (Ornitz et al., *J. Biol. Chem.* 271(25):15292–15297, 1996.)

There are four known extracellular FGF receptors (FGFRs), and they are all tyrosine kinases. In general, the FGF family members bind to all of the known FGFRs, however, specific FGFs bind to specific receptors with higher degrees of affinity. Another means for specificity within the FGF family is the spatial and temporal expression of the ligands and their receptors during embryogenesis. Evidence suggests that the FGFs most likely act only in autocrine and/or paracrine manner, due to their heparin binding affinity, which limits their diffusion from the site of release (Flaumenhaft et al., *J. Cell. Biol.* 111(4):1651–1659, 1990.) Basic FGF lacks a signal sequence, and is therefore restricted to paracrine or autocrine modes of action. It has been postulated that basic FGF is stored intracellularly and released upon tissue damage. Basic FGF has been shown to have two receptor binding regions that are distinct from the heparin binding site (Abraham et al.,. *EMBO J.* 5(10):2523–2528, 1986.)

It has been shown that FGFR-3 plays a role in bone growth. Mice made homozygous null for the FGFR-3 (−/−) resulted in postnatal skeletal abnormalities (Colvin et al., *Nature Genet.* 12:309–397, 1996 and Deng et al., *Cell* 84:911–921, 1996). The mutant phenotype suggests that in normal mice, FGFR-3 plays a role in regulation of chondrocyte cell division in the growth plate region of the bone (Goldfarb, *Cytokine and Growth Factor Rev.* 7(4):311–325, 1996). The ligand for the FGFR-3 in the bone growth plate has not been identified.

Although four FGFRs have been identified, all of which have been shown to have functional splice variants, the possibility that novel FGF receptors exist is quite likely. For example, no receptor has been identified for the FGF-8a isoform (MacArthur et al., *J. Virol.* 69(4):2501–2507, 1995.).

FGF-8 is a member of the FGF family that was originally isolated from mammary carcinoma cells as an androgen-inducible mitogen. It has been mapped to human chromosome 10q25–q26 (White et al., *Genomics* 30:109–11, 1995.) FGF-8 is involved in embryonic limb development (Vogel et al., *Development* 122:1737–1750, 1996 and Tanaka et al., *Current Biology* 5(6):594–597, 1995.) Expression of FGF-8 during embryogenesis in cardiac, urogenital and neural tissue indicates that it may play a role in development of these tissues (Crossley et al., *Development* 121:439–451, 1995.) There is some evidence that acrocephalosyndactylia, a congenital condition marked by peaked head and webbed fingers and toes, is associated with FGF-8 point mutations (White et al., 1995, ibid.)

FGF-8 has five exons, in contrast to the other known FGFs, which have only three exons. The first three exons of FGF-8 correspond to the first exon of the other FGFs (MacArthur et al., *Development* 121:3603–3613, 1995.) The human gene for FGF-8 codes for four isoforms which differ in their N-terminal regions: FGF isoforms a, b, e, and f; in contrast to the murine gene which gives rise to eight FGF-8 isoforms (Crossley et al., 1995, ibid.) Human FGF-8a and FGF-8b have 100% homology to the murine proteins, and FGF-8e and FGF-8f proteins are 98% homologous between human and mouse (Gemel et al., *Genomics* 35:253–257, 1996.)

Heart disease is the major cause of death in the United States, accounting for up to 30% of all deaths. Myocardial infarction (MI) accounts for 750,000 hospital admissions per year in the U.S., with more than 5 million people diagnosed with coronary disease. Risk factors for MI include diabetes mellitus, hypertension, truncal obesity, smoking, high levels of low density lipoprotein in the plasma or genetic predisposition.

Cardiac hyperplasia is an increase in cardiac myocyte proliferation, and has been demonstrated to occur with normal aging in the human and rat (Olivetti et al., *J. Am. Coll. Cardiol.* 24(1):140–9, 1994 and Anversa et al., *Circ. Res.* 67:871–885, 1990), and in catecholamine-induced cardiomyopathy in rats (Deisher et al., *Am. J. Cardiovasc. Pathol.* 5(1):79–88, 1994.) Whether the increase in myocytes originate with some progenitor, or are a result of proliferation of a more terminally differentiated cell type, remains controversial.

However, because infarction and other causes of myocardial necrosis appear to be irreparable, it appears that the normal mechanisms of cardiac hyperplasia cannot compensate for extensive myocyte death and there remains a need for exogenous factors that promote hyperplasia and ultimately result in renewal of the heart's ability to function.

Bone remodeling is the dynamic process by which tissue mass and skeletal architecture are maintained. The process is a balance between bone resorption and bone formation, with two cell types thought to be the major players. These cells are the osteoblast and osteoclast. Osteoblasts synthesize and deposit matrix to become new bone. The activities of osteoblasts and osteoclasts are regulated by many factors, systemic and local, including growth factors.

While the interaction between local and systemic factors has not been completely elucidated, there does appear to be consensus that growth factors play a key role in the regulation of both normal skeletal remodeling and fracture repair. Some of the growth factors that have been identified in bone include: IGF-I, IGF-II, TGF-$\beta_1$, TGF-$\beta_2$, bFGF, aFGF, PDGF and the family of bone morphogenic proteins (Baylink et al., *J. Bone Mineral Res.* 8 (Supp. 2):S565–S572, 1993).

When bone resorption exceeds bone formation, a net loss in bone results, and the propensity for fractures is increased. Decreased bone formation is associated with aging and certain pathological states. In the U.S. alone, there are approximately 1.5 million fractures annually that are attributed to osteoporosis. The impact of these fractures on the quality of the patient's life is immense. Associated costs to the health care system in the U.S. are estimated to be $5–$10 billion annually, excluding long-term care costs.

Other therapeutic applications for growth factors influencing bone remodeling include, for example, the treatment of injuries which require the proliferation of osteoblasts to heal, such as fractures, as well as stimulation of mesenchymal cell proliferation and the synthesis of intramembraneous bone which have been indicated as aspects of fracture repair (Joyce et al. 36th Annual Meeting, Orthopaedic Research Society, February 5–8, 1990. New Orleans, La.).

The present invention provides such polypeptides for these and other uses that should be apparent to those skilled in the art from the teachings herein.

SUMMARY OF THE INVENTION

Within one aspect, the present invention provides an isolated polynucleotide molecule encoding a fibroblast growth factor (FGF) homolog polypeptide selected from the group consisting of: a) polynucleotide molecules comprising a nucleotide sequence as shown in SEQ ID NO: 1 from nucleotide 82 to nucleotide 621; b) allelic variants of (a); c) polynucleotide molecules that encode a polypeptide that is at least 60% identical to the amino acid sequence of SEQ ID NO: 2 from amino acid residue 28 (Glu) to amino acid residue 207 (Ala); and d) polynucleotide molecules comprising a nucleotide sequence as shown in SEQ ID NO: 6 from nucleotide 82 to nucleotide 621.

In one embodiment, the isolated polynucleotide molecule comprises a nucleotide sequence as shown in SEQ ID NO: 1 from nucleotide 1 to nucleotide 621 or a nucleotide sequence as shown in SEQ ID NO: 6 from nucleotide 1 to nucleotide 621.

In another embodiment, the isolated polynucleotide molecule comprises a nucleotide sequence as shown in SEQ ID NO: 1 from nucleotide 82 to nucleotide 621.

In another aspect, the present invention provides an expression vector comprising the following operably linked elements: a transcription promoter; a DNA segment selected from the group consisting of: a) polynucleotide molecules comprising a nucleotide sequence as shown in SEQ ID NO: 1 from nucleotide 82 to nucleotide 621; b) allelic variants of (a); c) polynucleotide molecules that encode a polypeptide that is at least 60% identical to the amino acid sequence of SEQ ID NO: 2 from amino acid residue 28 (Glu) to amino acid residue 207 (Ala); and d) polynucleotide molecules comprising a nucleotide sequence as shown in SEQ ID NO: 6 from nucleotide 82 to nucleotide 621; and a transcription terminator.

In another aspect, the present invention provides a cultured cell into which has been introduced an expression vector comprising the following operably linked elements: a transcription promoter; a DNA segment selected from the group consisting of: a) polynucleotide molecules comprising a nucleotide sequence as shown in SEQ ID NO: 1 from nucleotide 82 to nucleotide 621; b) allelic variants of (a); c) polynucleotide molecules that encode a polypeptide that is at least 60% identical to the amino acid sequence of SEQ ID NO: 2 from amino acid residue 28 (Glu) to amino acid residue 207 (Ala); and d) polynucleotide molecules comprising a nucleotide sequence as shown in SEQ ID NO: 6 from nucleotide 82 to nucleotide 621; and a transcription terminator, wherein said cell expresses a polypeptide encoded by the DNA segment.

In another aspect, the present invention provides a method of producing an FGF homolog polypeptide comprising: culturing a cell into which has been introduced an expression vector comprising the following operably linked elements: a transcription promoter; a DNA segment selected from the group consisting of: a) polynucleotide molecules comprising a nucleotide sequence as shown in SEQ ID NO: 1 from nucleotide 82 to nucleotide 621; b) allelic variants of (a); c) polynucleotide molecules that encode a polypeptide that is at least 60% identical to the amino acid sequence of SEQ ID NO: 2 from amino acid residue 28 (Glu) to amino acid residue 207 (Ala); and d) polynucleotide molecules comprising a nucleotide sequence as shown in SEQ ID NO: 6 from nucleotide 82 to nucleotide 621; and a transcription terminator, whereby said cell expresses a FGF homolog polypeptide encoded by the DNA segment; and recovering the FGF homolog polypeptide.

In another aspect, the present invention provides an isolated FGF homolog polypeptide selected from the group consisting of: a) polypeptide molecules comprising an amino acid sequence as shown in SEQ ID NO: 2 from residue 28 (Glu) to residue 175 (Met); b) allelic variants of (a); and c) polypeptide molecules that are at least 60% identical to SEQ ID NO: 2 from amino acid residue 28 (Glu) to amino acid residue 175 (Met).

In another aspect, the present invention provides an isolated FGF homolog polypeptide selected from the group consisting of: a) polypeptide molecules comprising an amino acid sequence as shown in SEQ ID NO: 2 from residue 28 (Glu) to residue 196 (Lys); b) allelic variants of (a); and c) polypeptide molecules that are at least 60% identical to SEQ ID NO: 2 from amino acid residue 28 (Glu) to amino acid residue 196 (Lys).

In another embodiment, the present invention provides an isolated FGF homolog polypeptide selected from the group consisting of: a) polypeptide molecules comprising an amino acid sequence as shown in SEQ ID NO: 2 from residue 28 (Glu) to residue 207 (Ala); b) allelic variants of (a); and c) polypeptide molecules that are at least 60% identical to the amino acids of SEQ ID NO: 2 from amino acid residue 28 (Glu) to amino acid residue 207 (Ala).

In an additional embodiment, the present invention provides an FGF homolog polypeptide further comprising a signal sequence.

In another embodiment, the present invention provides an FGF homolog polypeptide further comprising a signal sequence as shown in SEQ ID NO: 2 from amino acid residue 1 (Met) to amino acid residue 27 (Ala).

The present invention also provides pharmaceutical composition comprising a purified FGF homolog polypeptide, in combination with a pharmaceutically acceptable vehicle.

In another aspect, the present invention provides an antibody that binds to an epitope of a polypeptide molecule comprising an amino acid sequence as shown in SEQ ID NO: 2 from residue 1 (Met) to residue 207 (Ala).

In another embodiment, the present invention provides an antibody that binds a polypeptide molecule comprising an amino acid sequence as shown in SEQ ID NO: 2 from residue 28 (Glu) to residue 196 (Lys).

In another aspect, the present invention provides a method of stimulating proliferation of myocytes or myocyte progenitors comprising administering to a mammal in need thereof, an amount of an FGF homolog polypeptide sufficient to produce a clinically significant increase in the number of myocytes or myocyte progenitors in said mammal.

In another embodiment, the present invention provides a method of stimulating proliferation of myocytes or myocyte progenitors, wherein the myocytes or myocyte progenitors are cardiac myocytes or cardiac myocytes progenitors.

In another aspect, the present invention provides a method for ex vivo stimulation of myocyte progenitor cells or myocytes comprising culturing heart tissue cells with an amount of an FGF homolog polypeptide sufficient to produce an increase in the number of myocyte progenitor cells or myocytes in the heart tissue cells cultured in the presence of an FGF homolog polypeptide, as compared to heart tissue myocyte progenitor cells or myocytes cultured in the absence of an FGF homolog polypeptide.

In another embodiment, the present invention provides a method for ex vivo stimulation of myocyte progenitor cells or myocytes, wherein the myocytes or myocyte progenitors are cardiac myocytes or cardiac myocytes progenitors.

In another aspect, the present invention provides a method of delivering an agent or drug selectively to heart tissue comprising: linking a first molecule comprising an FGF homolog polypeptide with a second molecule comprising an agent or drug to form a chimera; and administering the chimera to heart tissue.

BRIEF DESCRIPTION OF THE DRAWINGS

FIG. 1 and FIG. 2 illustrate a multiple alignment of human fibroblast growth factor homologous factor 1 (FHF-1; SEQ ID NO: 21), human myocyte-activating factor (FGF-10; SEQ ID NO: 22), human fibroblast growth factor homologous factor 4 (FHF-4; SEQ ID NO: 23), human fibroblast growth factor homologous factor 2 (FHF-2; SEQ ID NO: 24), human fibroblast growth factor homologous factor 3 (FHF-3; SEQ ID NO: 25), human FGF-4 (SEQ ID NO: 26), human FGF-6 (SEQ ID NO: 27), human FGF-2 (basic; SEQ ID NO: 28), human FGF-1 (acidic; SEQ ID NO: 29), human keratinocyte growth factor 2 (KGF-2; SEQ ID NO: 30), human keratinocyte growth factor precursor (FGF-7; SEQ ID NO: 31), human ZFGF-5 (SEQ ID NO: 2), human FGF-8 (SEQ ID NO: 32), human FGF-5 (SEQ ID NO: 33), human FGF-9 (SEQ ID NO: 34), and human FGF-3 (SEQ ID NO: 35). "*" designates conserved amino acids; ":" designates conserved amino acid substitutions; and "." designates less stringently conserved amino acid substitutions.

FIG. 3 is an inter-family similarity matrix illustrating the percent identity between: (1) human FGF-5 (SEQ ID NO: 33), (2) human FGF-6 (SEQ ID NO: 27), (3) human FGF-7 (SEQ ID NO: 31), (4) human FGF-8 (SEQ ID NO: 32), (5) human FGF-9 (SEQ ID NO: 34), (6) human zFGF5 (SEQ ID NO: 2), (7) human FGF-10 (SEQ ID NO: 22), (8) human FGF-1 (SEQ ID NO: 29), (9) human FHF-1 (SEQ ID NO: 21), (10) human FGF-2 (SEQ ID NO: 28), (11) human FHF-2 (SEQ ID NO: 24), (12) human FHF-4 (SEQ ID NO: 23), (13) human FGF-3 (SEQ ID NO: 35), (14) human KGF-2 (SEQ ID NO: 30), (15) human FHF-3 (SEQ ID NO: 25), and (16) human FGF-4 (SEQ ID NO: 26).

DETAILED DESCRIPTION OF THE INVENTION

The term "ortholog" (or "species homolog") denotes a polypeptide or protein obtained from one species that has homology to an analogous polypeptide or protein from a different species.

The term "paralog" denotes a polypeptide or protein obtained from a given species that has homology to a distinct polypeptide or protein from that same species.

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature 316:774–78, 1985). When applied to a protein, the term "isolated" indicates that the protein is found in a condition other than its native environment, such as apart from blood and animal tissue. In a preferred form, the isolated protein is substantially free of other proteins, particularly other proteins of animal origin. It is preferred to provide the protein in a highly purified form, i.e., greater than 95% pure, more preferably greater than 99% pure.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Most nuclear receptors also exhibit a multi-domain structure, including an amino-terminal, transactivating domain, a DNA binding domain and a ligand binding domain. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The present invention is based in part upon the discovery of a novel DNA sequence that encodes a fibroblast growth factor (FGF) homolog polypeptide having homology to FGF-8. Analysis of the tissue distribution of the mRNA corresponding to this novel DNA showed that expression was highest in fetal heart tissue and adult heart tissue, followed by apparent but decreased expression levels in fetal lung, skeletal muscle, smooth muscle tissues such as small intestine, colon and trachea. The FGF homolog polypeptide has been designated zFGF-5.

The novel zFGF-5 polypeptides of the present invention were initially identified by querying an EST database for growth factors. A single EST sequence was discovered and predicted to be related to the FGF family. The novel FGF homolog polypeptide encoded by the full length cDNA contained a motif of the formula: CXFXEX{6}Y (SEQ ID NO:36), wherein X is any amino acid and X{} is the number of X amino acids greater than one. This motif occurs in all known members of the FGF family and is unique to these proteins.

The nucleotide sequence of the zFGF-5 cDNA is described in SEQ ID NO. 1, and its deduced amino acid sequence is described in SEQ ID NO. 2. When amino acid residue 28 (Glu) to amino acid residue 181 (Gln) of SEQ ID NO: 2 is compared to the corresponding region of FGF-8 (See FIGS. 1 and 2) the aligned and deduced amino acid sequence has approximately 56% identity.

The novel polypeptide encoded by the polynucleotide described herein contains the CXFXE{6}Y motif present in all members of the FGF family. The CXFXE{6}Y (SEQ ID NO:36) motifs are highly conserved. A consensus amino acid sequence of the CXFXEX{6}Y (SEQ ID NO: 36) domain includes human fibroblast growth factor homologous factor 1 (FHF-1; Smallwood et al., *Proc. Natl. Acad. Sci. USA* 93:9850–9857, 1996), human myocyte-activating factor (FGF-10; HSU76381, GENBANK identifier, http://www.ncbi.nlm.nih.gov/ ), human fibroblast growth factor homologous factor 4 (FHF-4; Smallwood et al., 1996, ibid.), human fibroblast growth factor homologous factor 2 (FHF-2; Smallwood et al., 1996, ibid.), human fibroblast growth factor homologous factor 3 (FHF-3; Smallwood et al., 1996, ibid.), human FGF-4 (Basilico et al., *Adv. Cancer Res.* 59:115–165,1992), human FGF-6 (Basilico et al., 1992, ibid.), human FGF-2 (basic; Basilico et al., 1992, ibid.), human FGF-1 (acidic; Basilico et al., 1992, ibid.), human keratinocyte growth factor 2 (KGF-2; HSU67918 GENBANK identifier, http://www.ncbi.nlm.nih.gov/), human keratinocyte growth factor precursor (FGF-7; Basilico et al., 1992, ibid.), human zFGF-5, human FGF-8 (Gemel et al., *Genomics* 35:253–257, 1996), human FGF-5 (Basilico et al., 1992, ibid.), human FGF-9 (Miyamoto et al., *Mol. Cell. Biol.* 13:4251–4259, 1993), and human FGF-3 (Basilico et al., 1992, ibid.)

Analysis of the cDNA encoding a zFGF-5 polypeptide (SEQ ID NO: 1) revealed an open reading frame encoding 207 amino acids (SEQ ID NO: 2) comprising a mature polypeptide of 180 amino acids (residue 28 to residue 207 of SEQ ID NO: 2). Multiple alignment of zFGF-5 with other known FGFs revealed a block of high percent identity corresponding to amino acid residue 127 (Cys) to amino acid residue 138 (Tyr), of SEQ ID NO: 2 and is shown in the Figure. Several of the members of the FGF family do not have signal sequences.

Members of the FGF family are characterized by heparin binding domains. A putative heparin-binding domain for zFGF-5 has been identified in the region of amino acid residue 148 (Gly) to amino acid residue 169 (Gln) of SEQ ID NO: 2. It is postulated that receptor-mediated signaling is initiated upon binding of FGF ligand complexed with cell-surface heparin sulfate proteoglycans. Many FGF family members can be placed into one of two related families on the basis of their structures and functions. aFGF and bFGF consist of three exons separated by two introns of variable length. FGF-8 consists of five exons, the first three of which correspond to the first exon of aFGF and bFGF. All the known FGF family members are spliced to form single polypeptides.

SEQ ID NO: 6 is a degenerate polynucleotide sequence that encompasses all polynucleotides that could encode the zFGF-5 polypeptide of SEQ ID NO: 2 (amino acids 1 or 28 to 207). Thus, zFGF-5 polypeptide-encoding polynucleotides ranging from nucleotide 1 or 82 to nucleotide 621 of SEQ ID NO: 6 are contemplated by the present invention. Also contemplated by the present invention are fragments and fusions as described above with respect to SEQ ID NO: 1, which are formed from analogous regions of SEQ ID NO: 6, wherein nucleotides 82 to 621 of SEQ ID NO: 6 correspond to nucleotides 82 to 621 of SEQ ID NO: 1, for the encoding a mature zFGF-5 molecule.

The symbols in SEQ ID NO: 6 are summarized in Table 1 below.

TABLE 1

| Nucleotide | Resolutions | Complement | Resolutions |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| C\|G | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO: 6, encompassing all possible codons for a given amino acid, are set forth in Table 2 below.

TABLE 2

| Amno Acid | Letter | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | J | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | — | TAA TAG TGA | TRR |
| Asn\|Asp | B | | RAY |
| Glu\|Gln | Z | | SAR |
| Any | X | | NNN |
| Gap | — | — | |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may have some incorrect amino acids, but one of ordinary skill in the art can easily identify such erroneous sequences by reference to the amino acid sequence of SEQ ID NO: 2.

The highly conserved amino acids in zFGF-5 can be used as a tool to identify new family members. To identify new family members in EST databases, the conserved CXFXEX{6}Y (SEQ ID NO:36) motif can be used. In another method using polynucleotide probes and hybridization methods, RNA obtained from a variety of tissue sources can be used to generate cDNA libraries and probe these libraries for new family members. In particular, reverse transcription-polymerase chain reaction (RT-PCR) can be used to amplify sequences encoding highly degenerate DNA primers designed from the sequences corresponding to amino acid residue 127 (Cys) to amino acid residue 138 (Tyr) of SEQ ID NO: 2.

Within preferred embodiments of the invention the isolated polynucleotides will serve as a probe and hybridize to similar sized regions of SEQ ID NO: 1 or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is at least about 0.02 M at pH 7 and the temperature is at least about 60° C.

As previously noted, the isolated polynucleotides of the present invention include DNA and RNA. Methods for isolating DNA and RNA are well known in the art. It is generally preferred to isolate RNA from cardiac tissue, although DNA can also be prepared using RNA from other tissues or isolated as genomic DNA. Total RNA can be prepared using guanidine HCl extraction followed by isolation by centrifugation in a CsCl gradient (Chirgwin et al., Biochemistry 18:52–94, 1979). Poly (A)$^+$ RNA is prepared from total RNA using the method of Aviv and Leder (Proc. Natl. Acad. Sci. USA 69:1408–1412, 1972). Complementary DNA (cDNA) is prepared from poly(A)$^+$ RNA using known methods. Polynucleotides encoding zFGF-5 polypeptides are then identified and isolated by, for example, hybridization or PCR.

The present invention further provides counterpart polypeptides and polynucleotides from other species (orthologs or paralogs). Of particular interest are zFGF-5 polypeptides from other mammalian species, including murine, rat, porcine, ovine, bovine, canine, feline, equine and other primate proteins. Identification of paralogs of the human sequence are particularly interesting because while 8 paralogs of murine FGF-8 have been identifed, only 4 human paralogs are known. Human paralogs or species homologs of the human proteins can be cloned using information and compositions provided by the present invention in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue or cell line. A zFGF-5-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to zFGF-5. Similar techniques can also be applied to the isolation of genomic clones.

Those skilled in the art will recognize that the sequences disclosed in SEQ ID NO: 1 and SEQ ID NO: 2 represent a single allele of the human zFGF-5 gene and polypeptide, and that allelic variation and alternative splicing are expected to occur. Allelic variants can be cloned by probing cDNA or genomic libraries from different individuals according to standard procedures. Allelic variants of the DNA sequence shown in SEQ ID NO: 1, including those containing silent mutations and those in which mutations result in amino acid sequence changes, are within the scope of the present invention, as are proteins which are allelic variants of SEQ ID NO: 2.

The present invention also provides isolated zFGF-5 polypeptides that are substantially homologous to the polypeptides of SEQ ID NO: 2 and their species homologs/orthologs. The term "substantially homologous" is used herein to denote polypeptides having 50%, preferably 60%, more preferably at least 80%, sequence identity to the sequences shown in SEQ ID NO: 2 or their orthologs or paralogs. Such polypeptides will more preferably be at least 90% identical, and most preferably 95% or more identical to SEQ ID NO: 2 or its orthologs or paralogs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter des). The percent identity is then calculated as:

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

$$\frac{\text{Total number of identical matches}}{[\text{length of the longer sequence plus the number of gaps introduced into the longer sequence in order to align the two sequences}]} \times 100$$

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 4) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), maltose binding protein (Kellerman and Ferenci, *Methods Enzymol.* 90:459–463, 1982; Guan et al., *Gene* 67:21–30, 1987), or other antigenic epitope or binding domain. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

TABLE 4

Conservative amino acid substitutions

| | |
|---|---|
| Basic: | arginine |
| | lysine |
| | histidine |

TABLE 4-continued

Conservative amino acid substitutions

| | |
|---|---|
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The proteins of the present invention can also comprise, in addition to the 20 standard amino acids, non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxyethyl-cysteine, hydroxyethylhomocysteine, nitroglutamine, homoglutamine, pipecolic acid, tert-leucine, norvaline, 2-azaphenylalanine, 3-azaphenylalanine, 4-azaphenylalanine, 4-fluorophenylalanine, 4-hydroxyproline, 6-N-methyl lysine, 2-aminoisobutyric acid, isovaline and α-methyl serine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations are carried out in a cell free system comprising an E. coli S30 extract and commercially available enzymes and other reagents. Proteins are purified by chromatography. See, for example, Robertson et al., J. Am. Chem. Soc. 113:2722, 1991; Ellman et al., Meth. Enzymol. 202:301, 1991; Chung et al., Science 259:806–09, 1993; and Chung et al., Proc. Natl. Acad. Sci. USA 90:10145–49, 1993). In a second method, translation is carried out in Xenopus oocytes by microinjection of mutated mRNA and chemically aminoacylated suppressor tRNAs (Turcatti et al., J. Biol. Chem. 271:19991–98, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., Biochem. 33:7470–76, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395–403, 1993).

Essential amino acids in the zFGF-5 polypeptides of the present invention can be identified according to procedures known in the art, such as site-directed mutagenesis or alanine-scanning mutagenesis (Cunningham and Wells, Science 244: 1081–1085, 1989). In the latter technique, single alanine mutations are introduced at every residue in the molecule, and the resultant mutant molecules are tested for biological activity (e.g., proliferation of cardiac myocytes or fibroblasts, or stimulation of bone formation) to identify amino acid residues that are critical to the activity of the molecule. See also, Hilton et al., J. Biol. Chem. 271:4699–4708, 1996. Sites of ligand-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306–312, 1992; Smith et al., J. Mol. Biol. 224:899–904, 1992; Wlodaver et al., FEBS Lett. 309:59–64, 1992. The identities of essential amino acids can also be inferred from analysis of homologies with related FGFs and are shown in FIGS. 1 and 2.

Analyses of the amino acid sequence of zFGF-5 revealed a dibasic site at the C-terminus of the polypeptide (amino acid residue 196–197 (Lys-Arg)). A C-terminally truncated polypeptide comprising an amino acid sequence as shown in SEQ ID NO: 2, from amino acid residue 28 (Glu) to amino acid residue 196 (Lys) was demonstrated to have biological activity. Dibasic amino acids, such as, Arg-X-X-Arg (wherein X is any amino acid residue), Arg-Arg or Lys-Arg; are subject to cleavage by several enzymes, including, but not limited to, thrombin and carboxypeptidases. Therefore, it is within the scope of the claims to make conservative changes at dibasic amino acid residues, in particular the dibasic residues at amino acid residues 196 and 197 (Lys and Arg, respectively) of SEQ ID NO: 2.

Based on analyses of the FGF family a C-terminally truncated molecule that comprises amino acid residue 28 (Glu) to residue 175 (Met) of SEQ ID NO: 2 may be biologically active. An intramolecular disulfide bond is predicted to occur between amino acid residue 109 (Cys) nd residue 129 (Cys) of SEQ ID NO: 2.

Based on homology alignments with FGF-1 and FGF-2 crystal structures (Eriksson et al., Prot. Sci. 2:1274, 1993), secondary structure predictions for beta strand structure of zFGF-5 correlates to amino acid residues 56–59, 64–69, 73–76, 85–92, 96–102, 106–111, 115–119, 128–134, 138–144, 149–155, and 173–177 of SEQ ID NO: 2. Amino acids critical for zFGF-5 binding to receptors can be identified by site-directed mutagenesis of the entire zFGF-5 polypeptide. More specifically, they can be identified using site-directed mutagenesis of amino acids in the zFGF-5 polypeptide which correspond to amino acid residues in acidic FGF (FGF1) and basic FGF (FGF2) identified as critical for binding of these FGFs to their receptors (Blaber et al., Biochem. 35:2086–2094, 1996). These amino acids include Tyr33, Arg53, Asn110, Tyr112, Lys119, Trp123, Leu149 and Met151 in human FGF2, and Tyr30, Arg50, Asn107, Tyr109, Lys116, Trp122, Leu148 and Leu150 in human FGF1, as shown in FIG. 1 and FIG. 2. The corresponding amino acids in zFGF-5, as shown in FIG. 1 and FIG. 2, would be Tyr58, Gly77, Asn136, Tyr138, Lys145, Trp149, Met175 and Arg177. One skilled in the art will recognize that other members, in whole or in part, of the FGF family may have structural or biochemical similarities to zFGF-5, and be substituted making such analyses. Such regions would be important for biological functions of the molecule.

Multiple amino acid substitutions can be made and tested using known methods of mutagenesis and screening, such as those disclosed by Reidhaar-Olson and Sauer (Science 241:53–57, 1988) or Bowie and Sauer (Proc. Natl. Acad. Sci. USA 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis methods as disclosed above can be combined with high-throughput, automated screening methods to detect activity of cloned, mutagenized polypeptides in host cells. Mutagenized DNA molecules that encode active polypeptides (e.g., cell proliferation) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 28 (Glu) to 196 (Lys) or residues 28 (Glu) to 207 (Ala) of SEQ ID NO: 2, allelic variants thereof, or biologically active fragments thereof, and retain the proliferative properties of the wild-type protein. Such polypeptides may also include additional polypeptide segments as generally disclosed above.

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al. (eds.), *Current Protocols in Molecular Biology,* John Wiley and Sons, Inc., N.Y., 1987, which are incorporated herein by reference.

In general, a DNA sequence encoding a zFGF-5 polypeptide of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zFGF-5 polypeptide into the secretory pathway of a host cell, a secretory signal sequence (also known as a leader sequence, prepro sequence or pre sequence) is provided in the expression vector. The secretory signal sequence may be the native sequence, or a chimera comprising a signal sequence derived from another secreted protein (e.g., t-PA and α-pre-pro secretory leader) or synthesized de novo. The secretory signal sequence is joined to the zFGF-5 DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

A universal acceptor plasmid that can be used to clone a DNA encoding any polypeptide of interest, including polypeptide fusions is disclosed. The acceptor plasmid is useful within a method for preparing a double stranded, circular DNA molecule. The method comprises the steps of (a) providing a double-stranded donor DNA fragment encoding a polypeptide of interest; (b) providing a double-stranded, linear acceptor plasmid having blunt first and second ends and comprising a selectable marker and replication sequence that are functional in *Saccharomyces cerevisiae,* wherein the acceptor plasmid is essentially free of DNA encoding the polypeptide of interest; (c) providing a first double-stranded DNA linker comprising a first segment identical in sequence to a first region of the acceptor plasmid and a second segment identical in sequence to a first region of the donor DNA fragment, wherein each of the first and second segments of the first linker is at least 10 bp in length; (d) providing a second double-stranded DNA linker comprising a first segment identical in sequence to a second region of the acceptor plasmid and a second segment identical in sequence to a second region of the donor DNA fragment, wherein each of the first and second segments of the second linker is at least 10 bp in length; and (e) combining the donor DNA fragment, acceptor plasmid, first DNA linker, and second DNA linker in a *Saccharomyces cerevisiae* host cell whereby the donor DNA fragment is joined to the acceptor plasmid by homologous recombination of the donor DNA, acceptor plasmid, and linkers to form a closed, circular plasmid. The acceptor plasmid further comprises a transcription promoter proximal to the first end, and the donor DNA fragment is operably linked to the transcription promoter within the closed, circular plasmid. The acceptor plasmid further comprises a DNA segment encoding a leader peptide and/or one or more DNA segments encoding a peptide tag, positioned such that these DNA segments are operably linked to the donor DNA fragment within the closed, circular plasmid. Within a preferred embodiment, the acceptor plasmid further comprises (a) a promoter, a DNA segment encoding a leader peptide, and a DNA segment encoding a first peptide tag, wherein the DNA segment encoding a leader peptide is positioned between the promoter and the DNA segment encoding a first peptide tag proximal to the first end of the acceptor plasmid, wherein the promoter, DNA segment encoding a leader peptide, and DNA segment encoding a first peptide tag are operably linked; and (b) a DNA segment encoding a second peptide tag proximal to the second end of the acceptor plasmid.

A method for preparing a double stranded, circular DNA molecule comprising the steps of (a) providing a plurality of overlapping, double-stranded donor DNA fragments which collectively encode a polypeptide of interest; (b) providing a double-stranded, linear acceptor plasmid having blunt first and second ends and comprising a selectable marker and replication sequence that are functional in *Saccharomyces cerevisiae,* wherein the acceptor plasmid is essentially free of DNA encoding the polypeptide of interest; (c) providing a first double-stranded DNA linker comprising a first segment identical in sequence to a first region of the acceptor plasmid and a second segment identical in sequence to a first region of one of the donor DNA fragments, wherein each of the first and second segments of the first linker is at least 10 bp in length; (d)

providing a second double-stranded DNA linker comprising a first segment identical in sequence to a second region of the acceptor plasmid and a second segment identical in sequence to a region of another of the donor DNA fragments, wherein each of the first and second segments of the second linker is at least 10 bp in length; and (e) combining the donor DNA fragments, acceptor plasmid, first DNA linker, and second DNA linker in a *Saccharomyces cerevisiae* host cell whereby the donor DNA fragments are joined to the acceptor plasmid by homologous recombination to form a closed, circular plasmid comprising a region encoding the polypeptide of interest is disclosed. The acceptor plasmid further comprises one or more of a transcription promoter, a DNA segment encoding a leader peptide, and one or more DNA segments encoding a peptide tag as disclosed above.

Fungal cells, including yeast cells, and particularly cells of the genera Saccharomyces or Pichia, are particularly preferred cells for hosts for producing zFGF-5 fragments or polypeptide fusions.

Other methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. Transformed cells are selected by phenotype determined by the selectable marker, commonly drug resistance or the ability to grow in the absence of a particular nutrient (e.g., leucine). An alternative preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondii*, and *Candida maltosa* are known in the art. A particularly preferred system utilizes *Pichia methanolica* (see, PCT application WO 9717450). For alternative transformation systems, see, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349, which is incorporated herein by reference. Methods for transforming Acremonium chrysogenum are disclosed by Sumino et al., U.S. Pat. No. 5,162,228, which is incorporated herein by reference. Methods for transforming Neurospora are disclosed by Lambowitz, U.S. Pat. No. 4,486,533, which is incorporated herein by reference.

Cultured mammalian cells are also preferred hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology*, John Wiley and Sons, Inc., N.Y., 1987), and liposome-mediated transfection (Hawley-Nelson et al., *Focus* 15:73, 1993; Ciccarone et al., *Focus* 15:80, 1993), which are incorporated herein by reference. The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978, which are incorporated herein by reference) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used.

Other higher eukaryotic cells can also be used as hosts, including insect cells, plant cells and avian cells. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463, which are incorporated herein by reference. The use of *Agrobacterium rhizogenes* as a vector for expressing genes in plant cells has been reviewed by Sinkar et al., *J. Biosci.* (*Bangalore*) 11:47–58, 1987.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Expressed recombinant zFGF-5 polypeptides (or chimeric zFGF-5 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods,* Pharmacia LKB Biotechnology, Uppsala, Sweden, 1988.

The polypeptides of the present invention can also be isolated by exploitation of their heparin binding properties. For a review, see, Burgess et al., *Ann. Rev. of Biochem.* 58:575–606, 1989. Members of the FGF family can be purified to apparent homogeneity by heparin-Sepharose affinity chromatography (Gospodarowicz et al., *Proc. Natl. Acad. Sci.* 81:6963–6967, 1984) and eluted using linear step gradients of NaCl (Ron et al., *J. Biol. Chem.* 268(4):2984–2988, 1993; *Chromatography: Principles & Methods,* pp. 77–80, Pharmacia LKB Biotechnology, Uppsala, Sweden, 1993; in "Immobilized Affinity Ligand Techniques", Hermanson et al., eds., pp. 165–167, Academic Press, San Diego, 1992; Kjellen et al., *Ann. Rev. Biochem.Ann. Rev. Biochem.* 60:443–474, 1991; and Ke et al., *Protein Expr. Purif.* 3(6):497–507, 1992.) Other purification methods include using immobilized metal ion adsorption (IMAC) chromatography to purify histidine-rich proteins. Briefly, a gel is first charged with divalent metal ions to form a chelate (E. Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol., Vol.* 182, "Guide to Protein Purification", M. Deutscher, (ed.), Acad. Press, San Diego, 1990, pp.529–39). Alternatively, a fusion of the polypeptide of interest and an affinity tag (e.g., polyhistidine, maltose-binding protein, an immunoglobulin domain) may be constructed to facilitate purification.

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

zFGF-5 polypeptides or fragments thereof may also be prepared through chemical synthesis. zFGF-5 polypeptides may be monomers or multimers; glycosylated or non-glycosylated; pegylated or non-pegylated; and may or may not include an initial methionine amino acid residue.

The activity of molecules of the present invention can be measured using a variety of assays that, for example, measure neogenesis or hyperplasia (i.e., proliferation) of cardiac cells based on the tissue specificity in adult heart. Additional activities likely associated with the polypeptides of the present invention include proliferation of endothelial cells, cardiomyocytes, fibroblasts, skeletal myocytes directly or indirectly through other growth factors; action as a chemotaxic factor for endothelial cells, fibroblasts and/or phagocytic cells; osteogenic factor; and factor for expanding mesenchymal stem cell and precursor populations.

Proliferation can be measured using cultured cardiac cells or in vivo by administering molecules of the claimed invention to the appropriate animal model. Generally, proliferative effects are seen as an increase in cell number and therefore, may include inhibition of apoptosis, as well as mitogenesis. Cultured cells include cardiac fibroblasts, cardiac myocytes, skeletal myocytes, human umbilical vein endothelial cells from primary cultures. Established cell lines include: NIH 3T3 fibroblast (ATCC No. CRL-1658), CHH-1 chum heart cells (ATCC No. CRL-1680), H9c2 rat heart myoblasts (ATCC No.

CRL-1446), Shionogi mammary carcinoma cells (Tanaka et al., *Proc. Natl. Acad. Sci.* 89:8928–8932, 1992) and LNCap.FGC adenocarcinoma cells (ATCC No. CRL-1740.) Assays measuring cell proliferation are well known in the art. For example, assays measuring proliferation include such assays as chemosensitivity to neutral red dye (Cavanaugh et al., *Investigational New Drugs* 8:347–354, 1990, incorporated herein by reference), incorporation of radiolabelled nucleotides (Cook et al., *Analytical Biochem.* 179:1–7, 1989, incorporated herein by reference), incorporation of 5-bromo-2'-deoxyuridine (BrdU) in the DNA of proliferating cells (Porstmann et al., *J. Immunol. Methods* 82:169–179, 1985, incorporated herein by reference), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988; 10 all incorporated herein by reference).

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors. The stage of a cell population's differentiation is monitored by identification of markers present in the cell population. Myocytes, osteoblasts, adipocytes, chrondrocytes, fibroblasts and reticular cells are believed to originate from a common mesenchymal stem cell (Owen et al., *Ciba Fdn. Symp.* 136:42–46, 1988).

Markers for mesenchymal stem cells have not been well identified (Owen et al., *J. of Cell Sci.* 87:731–738, 1987), so identification is usually made at the progenitor and mature cell stages. The existence of early stage cardiac myocyte progenitor cells (often referred to as cardiac myocyte stem cells) has been speculated, but not demonstrated, in adult cardiac tissue. The novel polypeptides of the present invention are useful for studies to isolate mesenchymal stem cells and cardiac myocyte progenitor cells, both in vivo and ex vivo.

There is evidence to suggest that factors that stimulate specific cell types down a pathway towards terminal differentiation or dedifferentiation, affects the entire cell population originating from a common precursor or stem cell. Thus, the present invention includes stimulating inhibition or proliferation of myocytes, smooth muscle cells, osteoblasts, adipocytes, chrondrocytes and endothelial cells. Molecules of the present invention may, while stimulating proliferation or differentiation of cardiac myocytes, inhibit proliferation or differentiation of adipocytes, by virtue of the affect on their common precursor/stem cells. Thus molecules of the present invention, have use in inhibiting chondrosarcomas, atherosclerosis, restenosis and obesity.

Assays measuring differentiation include, for example, measuring cell-surface markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses*, 161–171, 1989; all incorporated herein by reference).

In vivo assays for evaluating cardiac neogenesis or hyperplasia include treating neonatal and mature rats with the molecules of the present invention. The animals cardiac function is measured as heart rate, blood pressure, and cardiac output to determine left ventricular function. Postmortem methods for assessing cardiac improvement include: increased cardiac weight, nuclei/cytoplasmic volume, staining of cardiac histology sections to determine proliferating cell nuclear antigen (PCNA) vs. cytoplasmic actin levels (Quaini et al., *Circulation Res.* 75:1050–1063, 1994 and Reiss et al., *Proc. Natl. Acad. Sci.* 93:8630–8635, 1996.)

In vivo assays for measuring changes in bone formation rates include performing bone histology (see, Recker, R., eds. *Bone Histomorphometry: Techniques and Interpretation.* Boca Raton: CRC Press, Inc., 1983) and quantitative computed tomography (QCT; Ferretti, J. *Bone* 17:353S–364S, 1995; Orphanoludakis et al., *Investig. Radiol.* 14:122–130,, 1979 and Durand et al., *Medical Physics* 19:569–573, 1992). An ex vivo assay for measuring changes in bone formation would be, for example, a calavarial assay (Gowen et al., *J. Immunol.* 136:2478–2482, 1986).

With regard to modulating energy balance, particularly as it relates to adipocyte metabolism, proliferation and differentiation, zFGF-5 polypeptides modulate effects on metabolic reactions. Such metabolic reactions include adipogenesis, gluconeogenesis, glycogenolysis, lipogenesis, glucose uptake, protein synthesis, thermogenesis, oxygen utilization and the like. Among other methods known in the art or described herein, mammalian energy balance may be evaluated by monitoring one or more of the aforementioned metabolic functions. These metabolic functions are monitored by techniques (assays or animal models) known to one of ordinary skill in the art, as is more fully set forth below. For example, the glucoregulatory effects of insulin are predominantly exerted in the liver, skeletal muscle and adipose tissue. In skeletal muscle and adipose tissue, insulin acts to stimulate the uptake, storage and utilization of glucose.

Art-recognized methods exist for monitoring all of the metabolic functions recited above. Thus, one of ordinary skill in the art is able to evaluate zFGF-5 polypeptides, fragments, fusion proteins, antibodies, agonists and antagonists for metabolic modulating functions. Exemplary modulating techniques are set forth below.

Insulin-stimulated lipogenesis, for example, may be monitored by measuring the incorporation of $^{14}$C-acetate into triglyceride (Mackall et al. *J. Biol. Chem.* 251:6462–6464, 1976) or triglyceride accumulation (Kletzien et al., *Mol. Pharmacol.* 41:393–398, 1992).

zFGF-5-stimulated uptake may be evaluated, for example, in an assay for insulin-stimulated glucose transport. Primary adipocytes or NIH 3T3 L1 cells (ATCC No. CCL-92.1) are placed in DMEM containing 1 g/l glucose, 0.5 or 1.0% BSA, 20 mM Hepes, and 2 mM glutamine. After two to five hours of culture, the medium is replaced with fresh, glucose-free DMEM containing 0.5 or 1.0% BSA, 20 mM Hepes, 1 mM pyruvate, and 2 mM glutamine. Appropriate concentrations of zFGF-5, insulin or IGF-1, or a dilution series of the test substance, are added, and the cells are incubated for 20–30 minutes. $^3$H or $^{14}$C-labeled deoxyglucose is added to ≈50 1M final concentration, and the cells are incubated for approximately 10–30 minutes. The cells are then quickly rinsed with cold buffer (e.g. PBS), then lysed with a suitable lysing agent (e.g. 1% SDS or 1 N NaOH). The cell lysate is then evaluated by counting in a scintillation counter. Cell-associated radioactivity is taken as a measure of glucose transport after subtracting non-specific binding as determined by incubating cells in the presence of cytocholasin b, an inhibitor of glucose transport. Other methods include those described by, for example, Manchester et al., *Am. J. Physiol.* 266 (*Endocrinol. Metab.* 29):E326–E333, 1994 (insulin-stimulated glucose transport).

Protein synthesis may be evaluated, for example, by comparing precipitation of $^{35}$S-methionine-labeled proteins following incubation of the test cells with $^{35}$S-methionine and $^{35}$S-methionine and a putative modulator of protein synthesis.

Thermogenesis may be evaluated as described by B. Stanley in *The Biology of Neuropeptide and Related Peptides,* W. Colmers and C. Wahlestedt (eds.), Humana ress, Ottawa, 1993, pp. 457–509; C. Billington et al., *Am. J. Physiol.* 260:R321, 1991; N. Zarjevski et al., *Endocrinolovy* 133:1753, 1993; C. Billington et al., *Am. J. Physiol.* 266:R1765, 1994; Heller et al., *Am. J. Physiol.* 252(4 Pt 2): R661–7, 1987; and Heller et al., *Am. J. Physiol.* 245(3): R321–8, 1983. Also, metabolic rate, which may be measured by a variety of techniques, is an indirect measurement of thermogenesis.

Oxygen utilization may be evaluated as described by Heller et al., *Pflugers Arch* 369(1): 55–9, 1977. This method also involved an analysis of hypothalmic temperature and metabolic heat production. Oxygen utilization and thermoregulation have also been evaluated in humans as described by Haskell et al., *J. Appl. Physiol.* 51(4): 948–54, 1981.

zFGF-5 polypeptides can also be used to prepare antibodies that specifically bind to zFGF-5 epitopes, peptides or polypeptides. Methods for preparing polyclonal and monoclonal antibodies are well known in the art (see, for example, Sambrook et al., *Molecular Cloning: A Laboratory Manual, Second Edition,* Cold Spring Harbor, N.Y., 1989; and Hurrell, J. G. R., Ed., *Monoclonal Hybridoma Antibodies: Techniques and Applications,* CRC Press, Inc., Boca Raton, Fla., 1982, which are incorporated herein by reference). As would be evident to one of ordinary skill in the art, polyclonal antibodies can be generated from a variety of warm-blooded animals, such as horses, cows, goats, sheep, dogs, chickens, rabbits, mice, and rats.

The immunogenicity of a zFGF-5 polypeptide may be increased through the use of an adjuvant, such as alum (aluminum hydroxide) or Freund's complete or incomplete adjuvant. Polypeptides useful for immunization also include fusion polypeptides, such as fusions of zFGF-5 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to zFGF-5 protein or peptide, and selection of antibody display libraries in phage or similar vectors (for instance, through use of immobilized or labeled zFGF-5 protein or peptide).

Antibodies are defined to be specifically binding if they bind to a zFGF-5 polypeptide with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art (for example, by Scatchard analysis).

A variety of assays known to those skilled in the art can be utilized to detect antibodies which specifically bind to zFGF-5 proteins or peptides. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant zFGF-5 protein or peptide.

Antibodies to zFGF-5 may be used for tagging cells that express zFGF-5; to target another protein, small molecule or chemical to heart tissue; for isolating zFGF-5 by affinity purification; for diagnostic assays for determining circulating levels of zFGF-5 polypeptides; for detecting or quantitating soluble zFGF-5 as marker of underlying pathology or disease; in analytical methods employing FACS; for screening expression libraries; for generating anti-idiotypic antibodies; and as neutralizing antibodies or as antagonists to block zFGF-5 mediated proliferation in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications.

Molecules of the present invention can be used to identify and isolate receptors involved in cardiac myocardial proliferation. For example, proteins and peptides of the present invention can be immobilized on a column and membrane preparations run over the column (*Immobilized Affinity Liqand Techniques,* Hermanson et al., eds., Academic Press, San Diego, Calif., 1992, pp.195–202). Proteins and peptides can also be radiolabeled (*Methods in Enzymol.,* vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified.

Antagonists will be useful for inhibiting the proliferative activities of zFGF-5 molecules, in cell types such as cardiac cells, including myocytes, fibroblasts and endothelial cells; osteoblasts and chondrocytes. Genes encoding zFGF-5 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB iotechnology Inc. (Piscataway, N.J.). Random peptide display libraries can be screened using the zFGF-5 sequences disclosed herein to identify proteins which bind to zFGF-5. These "binding proteins" which interact with zFGF-5 polypeptides may be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as zFGF-5 "antagonists" to block zFGF-5 binding and signal transduction in vitro and in vivo. These anti- zFGF-5 binding proteins would be useful for inhibiting expression of genes which result in proliferation or differentiation. Such anti-zFGF-5 binding proteins can be used for treatment, for example, in rhabdomyosarcoma, cardiac myxoma, bone cancers of osteoblast origin, and dwarfism, arthritis, ligament and cartilage repair, alone or combination with other therapies.

The molecules of the present invention will be useful for proliferation of cardiac tissue cells, such as cardiac myocytes or myoblasts; skeletal myocytes or myoblasts and smooth muscle cells; chrondrocytes; endothelial cells; adipocytes and osteoblasts in vitro. For example, molecules of the present invention are useful as components of defined cell culture media, and may be used alone or in combination with other cytokines and hormones to replace serum that is commonly used in cell culture. Molecules of the present invention are particularly useful in specifically promoting the growth and/or development of myocytes in culture, and may also prove useful in the study of cardiac myocyte hyperplasia and regeneration.

The polypeptides, nucleic acid and/or antibodies of the present invention may be used in treatment of disorders associated with myocardial infarction, congestive heart failure, hypertrophic cardiomyopathy and dilated cardiomyopathy. Molecules of the present invention may also be useful for limiting infarct size following a heart attack, promoting angiogenesis and wound healing following angioplasty or endarterectomy, to develop coronary collateral circulation, for revascularization in the eye, for complications related to poor circulation such as diabetic foot ulcers, for stroke, following coronary reperfusion using pharmacologic methods and other indications where angiogenesis is of benefit. Molecules of the present invention may be useful for improving cardiac function, either by inducing cardiac myocyte neogenesis and/or hyperplasia, by inducing coronary collateral formation, or by inducing remodelling of necrotic myocardial area. Other therapeutic uses for the present invention include induction of skeletal muscle neogenesis and/or hyperplasia, kidney regeneration and/or for treatment of systemic and pulmonary hypertension.

zFGF-5 induced coronary collateral development is measured in rabbits, dogs or pigs using models of chronic coronary occlusion (Landau et al., *Amer. Heart J.* 29:924–931, 1995; Sellke et al., Surgery 120(2) :182–188, 1996 and Lazarous et al., 1996, ibid.) zFGF-5 benefits for treating stroke is tested in vivo in rats utilizing bilateral carotid artery occlusion and measuring histological changes, as well as maze performance (Gage et al., *Neurobiol. Aging* 9:645–655, 1988). zFGF-5 efficacy in hypertension is tested in vivo utilizing spontaneously hypertensive rats (SHR) for systemic hypertension (Marche et al., *Clin. Exp. Pharmacol. Physiol. Suppl.* 1:S114–116, 1995).

Molecules of the present invention can be used to target the delivery of agents or drugs to the heart. For example, the molecules of the present invention will be useful limiting expression to the heart, by virtue of the tissue specific expression directed by the zFGF-5 promoter. For example, heart-specific expression can be achieved using a zFGF-5- adenoviral discistronic construct (Rothmann et al., Gene Therapy 3:919–926, 1996). In addition, the zFGF-5 polypeptides can be used to restrict other agents or drugs to heart tissue by linking ZFGF-5 polypeptides to another protein (Franz et al., *Circ. Res.* 73:629–638, 1993) by linking a first molecule that is comprised of a zFGF-5 homolog polypeptide with a second agent or drug to form a chimera. Proteins, for instance antibodies, can be used to form chimeras with zFGF-5 molecules of the present invention (Narula et al., *J. Nucl. Cardiol.* 2:26–34, 1995). Examples of agents or drugs include, but are not limited to, bioactive-polypeptides, genes, toxins, radionuclides, small molecule pharmaceuticals and the like. Linking may be direct or indirect (e.g., liposomes), and may occur by recombinant means, chemical linkage, strong non-covalent interaction and the like.

In one embodiment of the present invention, a composition comprising zFGF-5 protein is used as a therapeutic agent to enhance osteoblast-mediated bone formation. The compositions and methods using the compositions of the invention may be applied to promote the repair of bone defects and deficiencies, such as those occurring in closed, open and non-union fractures; to promote bone healing in plastic surgery; to stimulate bone ingrowth into non-cemented prosthetic joints and dental implants; in the treatment of periodontal disease and defects; to increase bone formation during distraction osteogenesis; and in treatment of other skeletal disorders that may be treated by stimulation of osteoblastic activity, such as osteoporosis and arthritis. De novo bone formation provided by the methods of the present invention will have use in repair of congenital, trauma-induced, oncologic resection of bone or healing bone following radiation-induced osteonecrosis (Hart et al, *Cancer* 37:2580–2585, 1976). The methods of the present invention may also find use in plastic surgery.

For pharmaceutical use, the proteins of the present invention are formulated for parenteral, particularly intravenous or subcutaneous, administration according to conventional methods. Intravenous administration will be by bolus injection or infusion over a typical period of one to several hours. In general, pharmaceutical formulations will include a zFGF-5 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in *Remington's Pharmaceutical Sciences,* Gennaro, ed., Mack Publishing Co., Easton Pa., 1990, which is incorporated herein by reference. Therapeutic doses will generally be in the range of 0.1 to 100 µg/kg of patient weight per day, preferably 0.5–20 µg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of zFGF-5 is an amount sufficient to produce a clinically significant change in myocyte proliferation, heart function, bone formation or increases in specific cell types associated with mesenchymal stem cells and progenitors for myocytes, osteoblasts and chrondocytes. In particular, a clinical significant increase in the number of myocytes or myocyte progenitor cells can be determined by measuring the left ventricular ejection fraction, prior to, and after administration of zFGF-5 molecules, and determining at least a 5% increase, preferably 10% or more, in the total ejection fraction. Tests to determine ejection fraction, as measured by blood ejected per beat, are well known to those ordinarily skilled in the art.

The invention is further illustrated by the following non-limiting examples.

EXAMPLES

Example 1

Extension of EST Sequence

Scanning of a translated DNA database using a query for growth factors resulted in identification of an expressed sequence tag (EST) sequence found to be a novel member of the FGF family, and designated ZFGF-5.

Oligonucleotide primers ZC11,676 (SEQ ID NO: 3) and ZC11,677 (SEQ ID NO: 4) were designed from the sequence of an expressed sequence tag (EST). The primers were used for priming internally within the EST, and when PCR was performed using MARATHON READY cDNA (Clontech, Palo Alto, Calif.) from adult heart tissue as template in polymerase chain reaction (PCR).

The conditions used for PCR were 1 cycle at 94° C. for 90 seconds, 35 cycles at 94° C. for 15 seconds; 68° C. for 1 minute; followed by 1 cycle for 10 minutes at 72° C. and 4° C. incubation period. The PCR reaction recreated 160 bp of the EST sequence, and confirmed that EST sequence was correct.

Other libraries that could be amplified with the oligo-nucleotide primers included skeletal muscle, lung, stomach, small intestine and thyroid.

Example 2

Tissue Distribution

Northerns were performed using Human Multiple Tissue Blots from Clontech (Palo Alto, Calif.). The 160 bp DNA fragment described in Example 1 was electrophoresed on a 1% agarose gel, the fragment was electroeluted, and then radioactively labeled using a randon priming MEGAPRIME DNA labeling system (Amersham, Arlington Heights, Ill.) according to the manufacturer's specifications. The probe was purified using a NUCTRAP push column (Stratagene Cloning Systems, La Jolla, Calif.). EXPRESSHYB (Clontech, Palo Alto, Calif.) solution was used for prehybridization and as a hydrizing solution for the Northern blots. Hybridization took place overnight at 68° C., and the blots were then washed in 2X SSC and 0.05% SDS at RT, followed by a wash in 0.1X SSC and 0.1% SDS at 50° C. A single band was observed at approximately 2.0 kb.

Signal intensity was highest for adult heart with relatively less intense signals in skeletal muscle and stomach.

Example 3

Assay for In Vitro Activity of zFGF-5

A.

The mitogenic activity of zFGF-5 is assayed using cell lines and cells from a primary culture. Conditioned medium from cells expressing the recombinant protein and/or purified protein is added to cultures of the following cell lines: NIH 3T3 fibroblast (ATCC No. CRL-1658), CHH-1 chum heart cells (ATCC No. CRL-1680), H9c2 rat heart myoblasts (ATCC No. CRL-1446), Shionogi mammary carcinoma cells (Tanaka et al., 1992, ibid.) and LNCaP.FGC adenocarcinoma cells. Freshly isolated cells useful for testing the proliferative activity of zFGF-5 include: cardiac fibroblasts, cardiac myocytes, skeletal myocytes and human umbilical vein endothelial cells.

Mitogenic activity is assayed by measurement of $^3$H-thymidine incorporation based on the method of Raines and Ross (*Meth. Enzymology* 109:749–773, 1985). Briefly, quiescent cells are plated cells at a density of $3 \times 10^4$ cells/ml in an appropriate medium. A typical growth medium is Dulbecco's Growth Medium (GIBCO-BRL, Gaithersburg, Md.) containing 10% fetal calf serum (FCS). The cells are cultured in 96-well plates and allowed to grow for 3–4 days. The growth medium is removed, and 180 μl of DFC (Table 5) containing 0.1% FCS is added per well. Half the wells have zFGF-5 protein added to them and the other half are a negative control, without zFGF-5. The cells are incubated for up to 3 days at 37° C. in 5% $CO_2$, and the medium is removed. One hundred microliters of DFC containing 0.1% FCS and 2 μCi/ml $^3$H-thymidine is added to each well, and the plates are incubated an additional 1–24 hours at 37° C. The medium is aspirated off, and 150 μl of trypsin is added to each well. The plates are incubated at 37° C. until the cells detached (at least 10 minutes). The detached cells are harvested onto filters using an LKB Wallac 1295-001 Cell Harvester (LKB Wallac, Pharmacia, Gaithersburg, Md.). The filters are dried by heating in a microwave oven for 10 minutes and counted in an LKB Betaplate 1250 scintillation counter (LKB Wallac) as described by the supplier.

TABLE 5

| | |
|---|---|
| 250 ml | Dulbecco's Modified Eagle's Medium (DMEM, Gibco-BRL) |
| 250 ml | Ham's F12 medium (Gibco-BRL) |
| 0.29 mg/ml | L-glutamine (Sigma, St. Louis, MO) |
| 1 mM | sodium pyruvate (Sigma, St. Louis, MO) |
| 25 mM | Hepes (Sigma, St. Louis, MO) |
| 10 μg/ml | fetuin (Aldrich, Milwaukee, WI) |
| 50 μg/ml | insulin (Gibco-BRL) |
| 3 ng/ml | selenium (Aldrich, Milwaukee, WI) |
| 20 μg/ml | transferrin (JRH, Lenexa, KS) |

B.

Hearts were isolated from 1 day old neonatal mice and then disrupted by repeat collagenase digestions, following the protocol of Brand et al., (*J. Biol. Chem.* 268:11500–11503, 1993). Individual myocytes were isolated over a Percoll gradient, and 2 ml were plated in 6 well tissue cultrue dishes at $0.5 \times 10^6$ cells/ml. Three days later the wells were washed 3 times with PBS without calcium or magnesium, and refed with 1 ml serum free medium (Table 6). The wells were inoculated with $10^{11}$ particles AdCMV-zFGF5 per well or AdCMV-GFP (green fluorescent protein) as a control, and incubated at 37° C. for 8 hours. The wells were then washed again 3 times with PBS without calcium or magnesium, and then refed with 2 mls serum free media.

Within 48 hours after inoculation with the AdCMV-zFGF5, the cultured myocytes have ceased to beat and have undergone a morphologic alteration, while the wells inoculated with the AdCMV-GFP continued to beat spontaneously and are unaffected morphologically by the inoculation. Wells incoulated with AdCMV-zFGF5 also contained, after 48, hours, a confluent layer of viable, non-adherent cells, without any loss in confluence of the adherent myocyte layers, indicating the proliferative activity of the adCMV-zFGF5 on cultured murine myocytes.

TABLE 6

DMEM
Ham's Nutrient Mixture F12 (Gibco-BRL; 1:1
mixture with DMEM)
17 mM NaHCO$_3$ (Sigma)
2 mM L-glutamine (Sigma)
1% PSN (Sigma)
1 μg/ml insulin
5 μg/ml transferrin
1 nM LiCl (Sigma)
1 nM selenium
25 μg/ml ascorbic acid(Sigma)
1 nM thyroxine (Sigma)

C.

zFGF-5 fused to a maltose binding protein (MBP), as described in Example 9A and purified as described in Example 10, was added to myocytes (Example 3B) at a concentration of 0.1 ng/ml MBP-zFGF5 was shown to stimulate proliferation of myocytes, as well.

Example 4

Assay for Ex Vivo Activity of zFGF-5

Cardiac mitogenesis is measured ex vivo by removing entire hearts from neonatal or 8-week old mice or rats. The excised heart is placed in Joklik's (Sigma, St. Louis, Mo.) or Dulbecco's medium at 37° C., 5% CO$_2$ for 4–24 hours. During the incubation period zFGF-5 polypeptide is added at a concentration range of 1 pg/ml to 100 μg/ml. Negative controls are using buffer only. $^3$H-thymidine is added and the samples are incubated for 1–4 hours, after which the heart is sectioned and mitogenesis is determined by autoradiography. Sections are used for histomorphometry to determine the nuclei/cytoplasmic volume (McLaughlin, *Am. J. Physiol.* 271:R122–R129, 1996.)

Alternatively, the heart was lyophilized and resuspended in 1 ml 0.1 N NaOH. The DNA was precipitated using ice cold 10% trichloroacetic acid (TCA). The supernatant was added to 9 ml scintillation fluid to measure non-specific $^3$H-thymidine incorporation. The resulting pellet was resuspended in 1 ml BTS-450 tissue solubilizer (Beckman, Fullerton, Calif.) and added to 9 ml of scintillation fluid to measure specific DNA incorporation of $^3$H-thymidine.

Left and right ventricles were isolated from isolated from 1 day old CD-1 mice (Jackson Labs, Bar Harbor, Me.), and incubated for 4 hours with 3 ng/ml zFGF5Hep2 (n=13; see Example 10) or control (n=10). $^3$H-thymidine was added for 1 hour. The ventricles were washed several times and then homogenized in 1 ml Joklik's medium. The resulting homogenate was added to 9 ml scintillation cocktail and analyzed for total $^3$H-thymidine uptake and DNA incorporation.

zFGF5-Hep2 increased H-thymidine uptake and incorporation in DNA 2.068±0.489 fold over control, indicating that zFGF5 is mitogenic for a cardiac cell.

Example 5

Assay for In Vivo Activity of zFGF-5

The proliferative effects of zFGF-5 are assayed in vivo using two-week old neonatal rats and/or two-month old adult rats. The rats are injected intraperiocardially either acutely or chronically.

A.

Neonatal rats are treated with zFGF-5 for 1 to 14 days over a dose range of 50 ng/day to 100 μg/day. After treatment, the effects of zFGF-5 versus the sham-treated animals is evaluated by measuring increased cardiac weight, improved in vivo and ex vivo left ventricular function, and by increased cardiac nuclear to cytosolic volume fractions, that are determined histomorphometrically.

B.

Rats with cardiomyopathy induced by chronic catecholamine infusion, by coronary ligation or for models of cardiomyopathy such as the Syrian Cardiomyopathic hamster (Sole et al., *Amer. J. Cardiol.* 62(11):20G–24G, 1988) are also used to evaluate the effects of zFGF-5 on cardiac function and tissue.

To induce cardiomyopathy using catecholamine, 7–8 week old rats are infused continuously with epinephrine for 2 weeks via osmotic minipumps implanted subcutaneously between their shoulder blades. The epinephrine infusion results in an increase in the left ventricular fibrotic lesion score from 0.005±0.005 to 2.11±0.18, scale from 0–3); increased left ventricular myocyte cell width from 17.36±0.46 μm to 23.05±0.62 μm; and negligible left ventricular papillary muscle contractile responses to isoproterenol (0.2 vs 1.1 grams tension compared to saline-infused rats. After the two week treatment period, the rats are injected intraperiocardially daily with either vehicle, zFGF-5, bFGF, IGF-I or IGF-II for up to 14 days. The rats are sacrificed and histomorphometry and histocytochemistry are performed.

Rats, treated as described above, are also evaluated at the end of the cathecholamine treatment, and again after growth factor treatment, where cardiac regeneration is measured as decreased left ventricular fibrotic lesion scores, reduced myocyte cell width and increased left ventricular papillary contractile responses to isoproterenol.

Example 6

Chromosomal Mapping of zFGF-5

ZFGF-5 was mapped to chromosome 5 using the commercially available version of the Whitehead Institute/MIT Center for Genome Research's "GeneBridge 4 Radiation Hybrid Panel" (Research Genetics, Inc., Huntsville, Ala.). The GeneBridge 4 Radiation Hybrid Panel contains DNAs suitable for PCR use from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of zFGF-5 with the "GeneBridge 4 RH Panel", 25 μl reactions were set up in a 96-well microtiter plate (Stratagene, La Jolla, Calif.) and used for PCR in a "RoboCycler Gradient 96" thermal cycler (Stratagene). Each of the 95 PCR reactions consisted of 2.5 μl 50X "Advantage KlenTaq Polymerase Mix" (Clontech), 2 μl dNTPs mix (2.5 mM each; Perkin-Elmer, Foster City, Calif.), 1.25 μl sense primer, ZC11,677 (SEQ ID NO: 4) 1.25 μl antisense primer, ZC12,053 (SEQ ID NO: 5).

2.5 μl "RediLoad" (Research Genetics, Inc), 0.5 μl "Advantage KlenTaq Polymerase Mix" (Clontech Laboratories, Inc.), 25 ng of DNA from an individual hybrid clone or control and ddH2O for a total volume of 25 μl. The reactions were overlaid with an equal amount of mineral oil and sealed. The PCR cycler conditions were as follows: an initial 1 cycle of 4 minutes at 94° C., 35 cycles of 1 minute at 94° C., 1.5 minute annealing at 66° C. and 1.5 minute extension at 72° C., followed by a final 1 cycle extension of 7 minutes at 72° C. The reactions were separated by electrophoresis on a 3% NuSieve GTG agarose gel (FMC Bioproducts, Rockland, Me.).

The results showed that zFGF-5 maps 541.12 cR from the top of the human chromosome 5 linkage group on the WICGR radiation hybrid map. Relative to the centromere, its nearest proximal marker was WI-16922 and its nearest distal marker was WI-14692. The use of surrounding CHLC map markers also helped position zFGF-5 in the 5q34-q35 region on the CHLC chromosome 5 version v8c7 integrated marker map (The Cooperative Human Linkage Center, www server-http://www.chlc.org/ChlcIntegratedMaps.html).

Example 7 zFGF-5 Effects on Bone

A.

An adenovirus vector containing the cDNA for zFGF-5 was contructed using methods described by Becker et al. (*Methods in Cell Biology* 43:161–189, 1994). Briefly, the cDNA for zFGF-5 (as shown in SEQ ID NO: 1) was cloned as a Xba I-Sal I fragment into pACCMV (Gluzman et al., *In Eucaryotic Viral Vectors,* Gluzman (eds.) pp.187–192, Cold Spring Harbor Press, Cold Springs Harbor N.Y., 1982). The pACCMV vector contains part of the adenovirus 5 genome, the CMV promoter and an SV40 terminator sequence. The plasmid containing the vector and cDNA insert was cotransfected with a plasmid containing the the adenovirus 5 genome, designated pJM17, (McGrory et al., *Virology* 163:614–617, 1988) into 293 cells (ATCC No. CRL-1573; American Type Culture Collection, Rockville, Md.), leading to a recombination event and the production of a recombinant adenovirus containing zFGF-5, designated AdCMV-zFGF5. The presence of the zFGF-5 cDNA was confirmed by PCR.

The adenovirus vector AdCMV-zFGF5 was used for gene tranfer in vivo by intravenous injection of between $1\times10^{11}$ and $5\times10^{11}$ particles/mouse. It has been shown that after intravenous injection, the majority of the virus targets the liver and very efficiently transduces hepatocytes (Herz et al., *Proc. Natl. Acad. Sci. USA* 90:2812–2816, 1993). It has been demonstrated that the cells produce the protein encoded by the cDNA, and in the case of secreted proteins, secret them into the circulation. High levels of expression and physiological effects have been demonstrated (Ohwada et al., *Blood* 88:768–774, 1996; Stevenson et al., *Arteriosclerosis, Thrombosis and Vascular Biology,* 15:479–484, 1995; Setoguchi et al., *Blood* 84:2946–2953, 1994; and Sakamoto et al., *Proc. Natl. Acad. Sci. USA* 91:12368–12372, 1994).

Six week old CD-1 mice (Jackson Labs, Bar Harbor, Me.) were treated with adenovirus containing no cDNA insert (AdCMV-null) or AdCMV-zFGF5 either IV through the tail vein or intrapericardially (IPC). A total of $5 \times 10^{11}$ viral particles/100 $\mu$l/mouse were given. 14 days after injection, the animals were sacrificed, and tibias and femurs were removed without being separated to examine any potential inflammatory response. The bones were fixed in 10% neutral buffered formalin and processed. They were decalcified in 5% formic acid with 10% sodium citrate, washed in water, dehydrated in a series of 70%–100% ethanol, cleared in xylene and embedded in paraffin. The specimens were cut longitudinally through both tibial and femoral metaphyses and stained with hemotoxylin and eosin for identification of bone cells. Osteoblasts were identified by central negative Golgi area and eccentric nucleus, while osteoclasts were identified by multinucleation, non-uniform shape and the Howship's lacunae associated with these resorbing cells.

For bone histomorphometry, femur samples were chosen. Cancellous bone volume was not measured due to variation in the sampling site (i.e., femur samples were not sectioned exactly at the same plane). Three bone parameters were evaluated for histomorphometric changes.

1. Number of endosteal osteoblasts: measured along the endosteal surface of cancellous bone at 180 X magnification in an area 1.22 mm proximal to the growth late.

2. Number of endosteal osteoclasts: measured along the endosteal surface of cancellous bone at 180 X magnification in an area 1.22 mm proximal to the growth plate.

3. Growth plate width: measured every 72 $\mu$m at 90 X magnification across the entire growth plate except at the peripheral ends to determine the growth plate activity.

Analyses of the data (mean±SD, n=4–7/group) demonstrated the following:

1. There appeared to be no detectable inlfammatory response at the joint between tibia and femur.

2. AdCMV-zFGF5 given IV or IPC in mice significantly increased osteogenic activity in the distal femural metaphysis, when examined at 2 weeks. This stimulation of osteogenic activity was indicated by:

a) significant increases in the number of endosteal osteoblasts in the cancellous bone of distal femurs following IV infusion or IPC injection of AdCMV-zFGF5, 530% and 263%, respectively, when compared with their relative vector only controls; and b) the observation of increased osteogenic tissues on the bone surface, suggesting increased differentiation of bone marrow stromal cells toward the osteoblast lineage.

3. The number of endosteal osteoclasts was not significantly affected by IV or IPC administration of AdCMV-zFGF5, when compared with their relative vector only controls.

4. The growth plate width was significantly decreased by IV infusion, but not IPC injection, of AdCMV-zFGF5, suggesting depressed growth plate activity following IV infusion. The differential effects of AdCMV-zFGF5 administrations have not been elucidated.

These results suggest that zFGF-5 is a strong mitogen for stimulation of osteoblast proliferation and that zFGF-5 has the capacity to induce new bone formation.

B.

Using essentially the same procedures described above in 7.A. QCT was done on female CD-1 (Jackson Labs) that were injected with $1\times10^{11}$ particles AdCMV-zFGF5 per mouse. The mice were sacrificed 30 days after injection and heart/tibial length ratios were increased compared to controls (injected with empty adenorvirus or saline). There were no differences between the groups in tibial lengths to account for the change, nor were there differences in any other organ weights among the groups. Thus, the indication is that zFGF-5 adenovirus selectively increases total bone density, trabecular bone density, and cortical thickness in the femur, as measured by QCT.

Example 8

Effects of zFGF-5 on Heart

As described in 7.B. CD-1 mice were given a single IV injection of AdCMV-zFGF5, sacrificed after four weeks, and the heart/tibial length ratios were found to be increased compared to empty adenovirus or saline treated mice. The results showed that there were no differences between the groups in tibial lengths to account for this change, nor were there differences in any other organ weights among the groups. This result suggests that AdCMV-zFGF5 selectively increased cardiac growth, when administered as an IV adenoviral construct.

Example 9

Expression of zFGF-5

A. Construction of zFGF5-Encoding Plasmids zFGF5, a fibroblast growth factor homolog, was expressed in *E. coli* using the MBP (maltose binding protein) fusion system from New England Biolabs (NEB; Beverly, Mass.). In this system, the zFGF5 cDNA was attached to the 3' end of the malE gene to form an MBP-zFGF5 fusion protein. Fusion protein expression was driven by the tac promoter; expression is "off" until the promoter is induced by addition of 1 mmol IPTG (isopropyl b-thiogalactosylpyranoside). Three variations of this fusion protein were made, differing only in their cleavage site for liberating zFGF5 from MBP. One construct had a thrombin cleavage site engineered between the MBP and zFGF5 domains. The second construct had a Factor Xa cleavage site, instead of a thrombin cleavage site. The third construct had an enterokinase cleavage site, instead of the thrombin cleavage site.

The constructs were built as in-frame fusions with MBP in accordance with the Multiple Cloning Site (MCS) of the pMAL-c2 vector (NEB), and according to the manufacturer's specifications. zFGF5 was amplified via PCR using primers which introduced convenient cloning sites, as well as cleavage sites using the following oligonucleotide primers: 1) for the thrombin construct: zc12,652 (SEQ ID NO: 7) and zc12,631 (SEQ ID NO: 8); 2) for the Factor Xa construct: zc15,290 (SEQ ID NO: 9) and zc12,631 (SEQ ID NO: 8); and 3) for the enterokinase construct: zc15,270 (SEQ ID NO: 10) and zc12,631 (SEQ ID NO: 8). In each case, the native zFGF5 signal sequence was not amplified; the zFGF5 as expressed begins at amino acid residue 26 of SEQ ID NO: 2 (Val was changed to an Ala). The thrombin construct was built by inserting an Xba I-Sal I zFGF5 fragment into the Xba I-Sal I sites of pMAL-c2. The Factor Xa construct was built by inserting a blunt-Sal I fragment into the Xmn I-Sal I sites of the MCS. The enterokinase construct was built by inserting an Xba I-Sal I fragment into the Xba-Sal I sites of pMAL-c2. Once the constructs were built, they were transformed into a variety of *E. coli* host strains and analyzed for high-level expression. The thrombin construct (designated pSDH90.5) was transfected into DH10B cells (GIBCO-BRL), while both the Factor Xa construct (designated pSDH117.3) and the enterokinase construct (designated pSDH116.3) were transfected into TOP10 cells (Invitrogen, San Diego, Calif.). All three MBP fusions are about 63 kD (43 kD in the MBP domain, and approximately 20 kD in the zFGF5 domain).

B. Homologous Recombination/ zFGF5

Expression of zFGF5 in *Pichia methanolica* utilizes the expression system described in co-assigned PCT WO 9717450, incorporated herein by reference. An expression plasmid containing all or part of a polynucleotide encoding zFGF5 is constructed via homologous recombination. The expression vector is built from pCZR204, which contains the AUG1 promoter, followed by the αFpp leader sequence, followed by an amino-terminal peptide tag, a blunt-ended SmaI restriction site, a carboxy-terminal peptide tag, a translational STOP codon, followed by the AUG1 terminator, the ADE2 selectable marker, and finally the AUG1 3' untranslated region. Also included in this vector are the URA3 and CEN-ARS sequences required for selection and replication in *S. cerevisisiae*, and the $Amp^R$ and colE1 ori sequences required for selection and replication in *E. coli*. The zFGF5 sequence inserted into this vector begins at residue 27 (Ala) of the zFGF amino acid sequence.

To construct pSDH114, a plasmid for expression of zFGF5 in *P. methanolica*, the following DNA fragments were transformed into *S. cerevisisae:* 100 ng of the 'acceptor vector' pCZR204 that has been digested with SmaI; 1 μg of an XbaI-SalI restriction fragment liberated from pSDH90.5 and encompassing zFGF5 coding sequence.; 1 μg of a synthetic, PCR-generated, double-stranded linker egment that spans 70 base pairs of the aFpp coding equence on one end and joins it to the 70 base pairs of he amino-terminus coding sequence from the mature zFGF5 sequence on the other was generated from the four oligonucleotides zc13,497 (SEQ ID NO: 11); zc15,131 (SEQ ID NO: 12); zc15,132; (SEQ ID NO: 18); zc15,134 (SEQ ID NO: 13), of which the sense strand of a double stranded sequence is shown in SEQ ID NO: 19 (5' linker sequence (aFpp→zFGF5 N-terminus)) and 1 μg of a synthetic, PCR-generated, double-stranded linker segment that spans 70 base pairs of carboxy terminus coding sequence from zFGF5 on one end with 70 base pairs of AUG1 terminator sequence was generated from the four oligonucleotides 13,529 (SEQ ID NO: 14); zc13,525 (SEQ ID NO: 15) zc13,526 (SEQ ID NO: 16); zc13,528 (SEQ ID NO: 17) of which the sense strand of a double stranded sense is shown in the SEQ ID NO: 20 (3' linker sequence (zFGF5 C-terminus→AUG1 terminator)). $Ura^+$ colonies were selected, and DNA from the resulting yeast colonies was extracted and transformed into *E. coli*. Individual clones harboring the correct expression construct were identified by PCR screening with oligonucleotides zc13,497 (SEQ ID NO: 11) and zc13,528 (SEQ ID NO: 12) followed by restriction digestion to verify the presence of the zFGF5 insert and DNA sequencing to confirm the desired DNA sequences had been enjoined with one another. Larger scale plasmid DNA is isolated for one of the correct clones, and the DNA is digested with Sfi I to liberate the Pichia-zFGF5 expression cassette from the vector backbone. The Sfi I-cut DNA is then transformed into a *Pichia methanolica* expression host, designated PMAD16, and plated on ADE D plates for selection. A variety of clones are picked and screened via Western blot for high-level zFGF5 expression.

More specifically, for small-scale protein production (e.g., plate or shake flask production), *P. methanolica* transformants that carry an expression cassette comprising a methanol-regulated promoter (such as the AUG1 promoter) are grown in the presence of methanol and the absence of interfering amounts of other carbon sources (e.g., glucose). For small-scale experiments, including preliminary screening of expression levels, transformants may be grown at 30° C. on solid media containing, for example, 20 g/L Bacto-agar (Difco), 6.7 g/L yeast nitrogen base without amino acids (Difco), 10 g/L methanol, 0.4 mg/L biotin, and 0.56 g/L of -Ade -Thr -Trp powder. Because methanol is a volatile carbon source it is readily lost on prolonged incubation. A continuous supply of methanol can be provided by placing a solution of 50% methanol in water in the lids of inverted plates, whereby the methanol is transferred to the growing cells by evaporative transfer. In general, not more than 1 ml of methanol is used per 100-mm plate. Slightly larger scale experiments can be carried out using cultures grown in shake flasks. In a typical procedure, cells are cultivated for two days on minimal methanol plates as disclosed above at 30° C., then colonies are used to inoculate a small volume of minimal methanol media (6.7 g/L yeast nitrogen base without amino acids, 10 g/L methanol, 0.4 mg/L biotin) at a cell density of about 1×10⁶ cells/ml. Cells are grown at 30° C. Cells growing on methanol have a high oxygen requirement, necessitating vigorous shaking during cultivation. Methanol is replenished daily (typically 1/100 volume of 50% methanol per day).

For production scale culturing, fresh cultures of high producer clones are prepared in shake flasks. The resulting cultures are then used to inoculate culture medium in a fermenter. Typically, a 500 ml culture in YEPD grown at 30° C. for 1–2 days with vigorous agitation is used to inoculate a 5-liter fermenter. The cells are grown in a suitable medium containing salts, glucose, biotin, and trace elements at 28° C., pH 5.0, and >30% dissolved $O_2$. After the initial charge of glucose is consumed (as indicated by a decrease in oxygen consumption), a glucose/methanol feed is delivered into the vessel to induce production of the protein of interest. Because large-scale fermentation is carried out under conditions of limiting carbon, the presence of glucose in the feed does not repress the methanol-inducible promoter.

Example 10

Purification of zFGF-5

*E.coli* fermentation medium was obtained from a strain expressing zfGFS as a Maltose Binding protein fusion (pSDH90.5, as described above). The MBPzFGF5 fusion was solubilized during sonication or French press rupture, using a buffer containing 20 mM Hepes, 0.4 M Nacl, 0.01 M EDTA, 10 mM DTT, at pH 7.4. The extraction buffer also included 5 µg/ml quantities of Pepstatin, Leupeptin, Aprotinin, Bestatin. Phenyl methyl sulfonylfluoride (PMSF) was also included at a final concentration of 0.5 mM.

The extract was spun at 18,000×g for 30 minutes at 4° C. The resulting supernatent was processed on an Amylose resin (Pharmacia LKB Biotechnology, Piscataway, N.J.) which binds the MBP domain of the fusion. Upon washing the column, the bound MBPzFGF5 fusion was eluted in the same buffer as extraction buffer without DTT and protease inhibitors but containing 10 mM Maltose.

The eluted pool of MBPZFGF5 was treated with 1:100 (w/w) Bovine thrombin to MBPZFGF5 fusion. The cleavage reaction was allowed to proceed for 6 to 8 hours at room temperature, after which the reaction mixture was passed over a bed of Benzamidine sepharose (Pharmacia LKB Biotechnology, Piscataway, N.J.) to remove the thrombin, using the same elution buffer as described above for Amylose affinity chromatography.

The passed fraction, containing the cleaved product ZFGF5 and free MBP domain were applied to a Toso Haas Heparin affinity matrix (Toso Haas, Montgomeryville, Pa.) equilibrated in 0.5 M NaCl, 20 mM Hepes, 0.01 M EDTA at pH 7.4. The MBP and ZFGF5 both bound to heparin under these conditions. The bound proteins were eluted with a 2 to 3 column volume gradient formed between 0.5M NaCl and 2.0 M NaCl in column buffer.

The MBP eluted early, at about 0.7 M NaCl, and the cleaved zFgf5 eluted at about 1.3 M NaCl. The pooled zFGF5 fractions were passed through the amylose step once again to remove any residual MBPzfgf5 that is a minor contaminant. The purified material was designated zFGF5-Hep2, and shows a single highly pure species at ~20 kDa on reducing SDS-PAGE analysis.

Amino acid N-terminal sequencing yielded the native N-Terminal sequence but Mass Spectrophotometry data revealed molecular masses indicating that the C-Terminus must be truncated at residue 196 (Lys) of SEQ ID NO: 2, where a "dibasic site" is present.

zFGF5 protein was very stable in 1.3 M NaCl. Upon dialysis into PBS, the zFGF5 aggregated and left the solution phase. Therefore,formulations that include heparin and other "polyanions" may be used to prevent the aggregation of pure zFGF5.

Example 11

Production of Antibodies

Antibodies for ZFGF5 were produced, using standard techniques known in the art and described previously, by immunizing guinea pigs, rabbits and mice with peptides QTRARDDVSRKQLRLYC (SEQ ID NO: 2 amino acid residue 40 to residue 56), designated zFGF-1; YTTVT-KRSRRIRPTHRAC (SEQ ID NO: 2 amino acid residue 191 to residue 207, with an additional Cys at the C-terminus), designated zFGF-5 or the full-length zFGF5 polypeptide as shown in SEQ ID NO: 2, plus the MPB fusion protein, and designated MBP-FGF5. Peptides were conjugated through Cys residues using Maleimide-activated KLH (Pierce Chemical Co., Rockford, Ill.).

TABLE 7

| Peptide or Protein | animal | immmun. level | Ab produced |
|---|---|---|---|
| ZFGF5-1 | G.P. | 50 ug/animal initial 25 ug/animal boost | Affinity purified and IgG fractionated |
|  | Rabbit | 100 ug/animal initial 50 ug/animal boost | Affinity purified and IgG fractionated |
| ZFGF5-2 | G.P. | 50 ug/animal initial 25 ug/animal boost | Affinity purified and IgG fractionated |
|  | Rabbit | 100 ug/animal initial 50 ug/animal boost | Affinity purified. and IgG fractionated |
| ZFGF5-MBP | Mouse | 20 ug/animal initial 10 ug/animal boost |  |
|  | Rabbit | 200 ug/animal initial 100 ug/animal boost | Affinity purified |

Example 12

Effects of zFGF-5 on ob/ob Mice

The effects of zFGF-5 on adipocytes and fat metabolism were examined using female ob/ob mice (C57B1/6J, Jackson Labs, Bar Harbor, Me.). The mice are obese, insulin resistant and have "fatty bone". The mice were weighed and all were found to be the same weight, and were injected IV with $10^{11}$ particles per mouse of AdCMVzFGF-5 or either saline or Ad5CMV-GFP for controls, as described in Example 7. 17 days after injection, the control mice injected with Ad5CMV-GFP had gained 5.342±0.5 grams of body weight compared to the day of injection, while the AdCMVzFGF-5 treated mice lost 3.183±0.743 grams of body weight.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

We claim:

1. An isolated polynucleotide molecule comprising a nucleotide sequence as shown in SEQ ID NO: 6 from nucleotide 82 to nucleotide 621 or its complement.

2. The isolated polynucleotide molecule of claim 1, wherein the polynucleotide is DNA.

3. An expression vector comprising the following operably linked elements:

a transcription promoter;

a polynucleotide according to claim 1 wherein the polynucleotide comprises a nucleotide sequence as shown in SEQ ID NO:6 from nucleotide 82 to nucleotide 621; and a transcription terminator.

4. A cultured cell into which has been introduced an expression vector according to claim 3, wherein said cell expresses a polypeptide encoded by the DNA segment.

5. A method of producing an FGF homolog polypeptide comprising:

culturing a cell into which has been introduced an expression vector according to claim 3, whereby said cell expresses a FGF homolog polypeptide encoded by the DNA segment; and recovering the FGF homolog polypeptide.

6. An isolated polynucleotide molecule, wherein the polynucleotide molecule comprises a nucleotide sequence as shown in SEQ ID NO: 1 from nucleotide 1 to nucleotide 621 or a nucleotide sequences as shown in SEQ ID NO: 6 from nucleotide 1 to nucleotide 621.

7. The isolated polynucleotide molecule of claim 1, wherein the polynucleotide molecule comprises a nucleotide sequence as shown in SEQ ID NO: 1 from nucleotide 82 to nucleotide 621.

8. An isolated polynucleotide molecule comprising a nucleotide sequence as shown in SEQ ID NO: 6 from nucleotide 82 to nucleotide 588 or its complement.

9. An isolated polynucleotide molecule comprising a polynucleotide sequence that encodes an FGF homolog polypeptide as shown in SEQ ID NO: 2 from amino acid residue 28 (Glu) to amino acid residue 207 (Ala).

10. An expression vector comprising the following operably linked elements:

a transcription promoter;

a polynucleotide according to claim 8 wherein the polynucleotide comprises a nucleotide sequence as shown in SEQ ID NO:6 from nucleotide 82 to nucleotide 588; and a transcription terminator.

11. A cultured cell into which has been introduced an expression vector according to claim 10, wherein said cell expresses a polypeptide encoded by the DNA segment.

12. The isolated polynucleotide of claim 9, wherein the polypeptide comprises an amino acid sequence as shown in SEQ ID NO:2 from amino acid residue 1 (Met) to amino acid residue 207 (Ala).

13. An isolated polynucleotide molecule, wherein the polynucleotide comprises a nucleotide sequence as shown in SEQ ID NO: 1 from nucleotide 82 to nucleotide 588 or its complement.

14. An isolated polynucleotide molecule comprising a polynucleotide sequence that encodes an FGF homolog polypeptide as shown in SEQ ID NO:2 from amino acid residue 28 (Glu) to amino acid residue 196 (Lys).

15. The isolated polynucleotide of claim 14, wherein the polypeptide comprises an amino acid sequence as shown in SEQ ID NO.2 from amino acid residue 1 (Met) to amino acid residue 196 (Lys).

* * * * *

SEQUENCE LISTING

<160> NUMBER OF SEQ ID NOS: 36

<210> SEQ ID NO 1
<211> LENGTH: 917
<212> TYPE: DNA
<213> ORGANISM: Homo sapiens
<220> FEATURE:
<221> NAME/KEY: CDS
<222> LOCATION: (1)...(621)

<400> SEQUENCE: 1

```
atg tat tca gcg ccc tcc gcc tgc act tgc ctg tgt tta cac ttc ctg      48
Met Tyr Ser Ala Pro Ser Ala Cys Thr Cys Leu Cys Leu His Phe Leu
 1               5                  10                  15 ctg ctg tgc ttc cag gta cag gtg ctg gtt gcc gag gag aac gtg gac      96
Leu Leu Cys Phe Gln Val Gln Val Leu Val Ala Glu Glu Asn Val Asp
            20                  25                  30 ttc cgc atc cac gtg gag aac cag acg cgg gct cgg gac gat gtg agc     144
Phe Arg Ile His Val Glu Asn Gln Thr Arg Ala Arg Asp Asp Val Ser
        35                  40                  45 cgt aag cag ctg cgg ctg tac cag ctc tac agc cgg acc agt ggg aaa     192
Arg Lys Gln Leu Arg Leu Tyr Gln Leu Tyr Ser Arg Thr Ser Gly Lys
    50                  55                  60 cac atc cag gtc ctg ggc cgc agg atc agt gcc cgc ggc gag gat ggg     240
His Ile Gln Val Leu Gly Arg Arg Ile Ser Ala Arg Gly Glu Asp Gly
65                  70                  75                  80 gac aag tat gcc cag ctc cta gtg gag aca gac acc ttc ggt agt caa     288
Asp Lys Tyr Ala Gln Leu Leu Val Glu Thr Asp Thr Phe Gly Ser Gln
                85                  90                  95 gtc cgg atc aag ggc aag gag acg gaa ttc tac ctg tgc atg aac cgc     336
Val Arg Ile Lys Gly Lys Glu Thr Glu Phe Tyr Leu Cys Met Asn Arg
            100                 105                 110 aaa ggc aag ctc gtg ggg aag ccc gat ggc acc agc aag gag tgt gtg     384
Lys Gly Lys Leu Val Gly Lys Pro Asp Gly Thr Ser Lys Glu Cys Val
        115                 120                 125 ttc atc gag aag gtt ctg gag aac aac tac acg gcc ctg atg tcg gct     432
Phe Ile Glu Lys Val Leu Glu Asn Asn Tyr Thr Ala Leu Met Ser Ala
    130                 135                 140 aag tac tcc ggc tgg tac gtg ggc ttc acc aag aag ggg cgg ccg cgg     480
Lys Tyr Ser Gly Trp Tyr Val Gly Phe Thr Lys Lys Gly Arg Pro Arg
145                 150                 155                 160 aag ggc ccc aag acc cgg gag aac cag cag gac gtg cat ttc atg aag     528
Lys Gly Pro Lys Thr Arg Glu Asn Gln Gln Asp Val His Phe Met Lys
                165                 170                 175 cgc tac ccc aag ggg cag ccg gag ctt cag aag ccc ttc aag tac acg     576
Arg Tyr Pro Lys Gly Gln Pro Glu Leu Gln Lys Pro Phe Lys Tyr Thr
            180                 185                 190 acg gtg acc aag agg tcc cgt cgg atc cgg ccc aca cac cct gcc          621
Thr Val Thr Lys Arg Ser Arg Arg Ile Arg Pro Thr His Pro Ala
        195                 200                 205 taggccaccc cgccgcggcc ctcaggtcgc cctggccaca ctcacactcc cagaaaactg     681
catcagagga atatttttac atgaaaaata aggatttat tgttgacttg aaaccccga       741 tgacaaaaga ctcacgcaaa gggactgtag tcaacccaca ggtgcttgtc tctctctagg    801
aacagacaac tctaaactcg tccccagagg aggacttgaa tgaggaaacc aacactttga    861
gaaaccaaag tccttttttcc caaggttcct gaaaaaaaaa aaaaaaaaaa ctcgag       917
```

<210> SEQ ID NO 2
<211> LENGTH: 207
<212> TYPE: PRT
<213> ORGANISM: Homo sapiens

<400> SEQUENCE: 2

```
Met Tyr Ser Ala Pro Ser Ala Cys Thr Cys Leu Cys Leu His Phe Leu
  1               5                  10                  15

Leu Leu Cys Phe Gln Val Gln Val Leu Val Ala Glu Glu Asn Val Asp
             20                  25                  30

Phe Arg Ile His Val Glu Asn Gln Thr Arg Ala Arg Asp Asp Val Ser
         35                  40                  45

Arg Lys Gln Leu Arg Leu Tyr Gln Leu Tyr Ser Arg Thr Ser Gly Lys
     50                  55                  60

His Ile Gln Val Leu Gly Arg Arg Ile Ser Ala Arg Gly Glu Asp Gly
 65                  70                  75                  80

Asp Lys Tyr Ala Gln Leu Leu Val Glu Thr Asp Thr Phe Gly Ser Gln
                 85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205
```

<210> SEQ ID NO 3
<211> LENGTH: 24
<212> TYPE: DNA
<213> ORGANISM: Artificial Sequence
<220> FEATURE:
<223> OTHER INFORMATION: oligonucleotide primer ZC11676

<400> SEQUENCE: 3
ggacttgact accgaaggtg tctg         24

<210> SEQ ID NO 4
<211> LENGTH: 23
<212> TYPE: DNA
<213> ORGANISM: Artificial Sequence
<220> FEATURE:
<223> OTHER INFORMATION: oligonucleotide primer ZC11677

<400> SEQUENCE: 4
gtcgatgtga gccgtaagca gct          23

<210> SEQ ID NO 5
<211> LENGTH: 26
<212> TYPE: DNA
<213> ORGANISM: Artificial Sequence
<220> FEATURE:
<223> OTHER INFORMATION: oligonucleotide primer ZC12053

-continued

<400> SEQUENCE: 5
gcatacttgt ccccatcctc gccgcg                                              26

<210> SEQ ID NO 6
<211> LENGTH: 621
<212> TYPE: DNA
<213> ORGANISM: Artificial Sequence
<220> FEATURE:
<221> NAME/KEY: variation
<222> LOCATION: (1)...(621)
<223> OTHER INFORMATION: degenerate sequence
<223> OTHER INFORMATION: n is any nucleotide

<400> SEQUENCE: 6
atgtaywsng cnccnwsngc ntgyacntgy ytntgyytnc ayttyytnyt nytntgytty         60
cargtncarg tnytngtngc ngargaraay gtngayttym gnathgaygt ngaraarcar        120
acnmgngcnm gngaygaygt nwsnmgnaar carytnmgny tntaycaryt ntaywsnmgn        180
acnwsnggna arcayathca rgtnytnggn mgnmgnathw sngcnmgngg ngargaygyn        240
gayaartayg cncarytnyt ngtngaracn gayacnttyg gnwsncargt nmgnathaar        300
ggnaargara cngarttyta yytntgyatg aaymgnaarg gnaarytngt nggnaarccn        360
gayggnacnw snaargartg ygtnttyath garaargtny tngaraayaa ytayacngcn        420
ytnatgwsng cnaartayws nggntggtay gtnggnttya cnaaraargg nmgnccnmgn        480
aarggnccna aracnmgnga raaycarcar gaygtncayt tyatgaarmg ntayccnaar        540
ggncarccng arytncaraa rccnttyaar tayacnacng tnacnaarmg nwsnmgnmgn        600
athmgnccna cncayccngc n                                                 621

<210> SEQ ID NO 7
<211> LENGTH: 47
<212> TYPE: DNA
<213> ORGANISM: Artificial Sequence
<220> FEATURE:
<223> OTHER INFORMATION: oligonucleotide primer ZC12652

<400> SEQUENCE: 7
tatttatcta gactggttcc gcgtgccgcc gaggagaacg tggactt                      47

<210> SEQ ID NO 8
<211> LENGTH: 33
<212> TYPE: DNA
<213> ORGANISM: Artificial Sequence
<220> FEATURE:
<223> OTHER INFORMATION: oligonucleotide primer ZC12631

<400> SEQUENCE: 8
gtatttgtcg actcaggcag ggtgtgtggg ccg                                     33

<210> SEQ ID NO 9
<211> LENGTH: 22
<212> TYPE: DNA
<213> ORGANISM: Artificial Sequence
<220> FEATURE:
<223> OTHER INFORMATION: oligonucleotide primer ZC15290

<400> SEQUENCE: 9
gccgaggaga acgtggactt cc                                                 22

<210> SEQ ID NO 10
<211> LENGTH: 47

-continued

```
<212> TYPE: DNA
<213> ORGANISM: Artificial Sequence
<220> FEATURE:
<223> OTHER INFORMATION: oligonucleotide primer ZC15270

<400> SEQUENCE: 10
tatttatcta gagatgacga tgacaaggcc gaggagaacg tggactt            47

<210> SEQ ID NO 11
<211> LENGTH: 41
<212> TYPE: DNA
<213> ORGANISM: Artificial Sequence
<220> FEATURE:
<223> OTHER INFORMATION: oligonucleotide primer ZC13497

<400> SEQUENCE: 11
agcattgcta aagaagaagg tgtaagcttg gacaagagag a                  41

<210> SEQ ID NO 12
<211> LENGTH: 63
<212> TYPE: DNA
<213> ORGANISM: Artificial Sequence
<220> FEATURE:
<223> OTHER INFORMATION: oligonucleotide primer ZC15131

<400> SEQUENCE: 12
ggtgtaagct tggacaagag agaggagaac gtggacttcc gcatccacgt ggagaaccag    60
acg                                                                 63

<210> SEQ ID NO 13
<211> LENGTH: 39
<212> TYPE: DNA
<213> ORGANISM: Artificial Sequence
<220> FEATURE:
<223> OTHER INFORMATION: oligonucleotide primer ZC15134

<400> SEQUENCE: 13
ccggctgtag agctggtaca gccgcagctg cttacggct                    39

<210> SEQ ID NO 14
<211> LENGTH: 42
<212> TYPE: DNA
<213> ORGANISM: Artificial Sequence
<220> FEATURE:
<223> OTHER INFORMATION: oligonucleotide primer ZC13529

<400> SEQUENCE: 14
cttcagaagc ccttcaagta cacgacggtg accaagaggt cc                42

<210> SEQ ID NO 15
<211> LENGTH: 61
<212> TYPE: DNA
<213> ORGANISM: Artificial Sequence
<220> FEATURE:
<223> OTHER INFORMATION: oligonucleotide primer ZC13525

<400> SEQUENCE: 15
acgacggtga ccaagaggtc ccgtcggatc cggcccacac accctgccta ggggaattc    60
g                                                                   61

<210> SEQ ID NO 16
<211> LENGTH: 61
<212> TYPE: DNA
<213> ORGANISM: Artificial Sequence
<220> FEATURE:
<223> OTHER INFORMATION: oligonucleotide primer ZC13526

<400> SEQUENCE: 16
```

```
caaacaggca gccctagaat actagtgtcg actcgaggat ccgaattccc cctaggcagg    60
g                                                                   61
```

<210> SEQ ID NO 17
<211> LENGTH: 44
<212> TYPE: DNA
<213> ORGANISM: Artificial Sequence
<220> FEATURE:
<223> OTHER INFORMATION: oligonucleotide primer ZC13528

<400> SEQUENCE: 17

```
ctcaaaaatt ataaaaatat ccaaacaggc agccctagaa tact                    44
```

<210> SEQ ID NO 18
<211> LENGTH: 186
<212> TYPE: DNA
<213> ORGANISM: Artificial Sequence
<220> FEATURE:
<223> OTHER INFORMATION: oligonucleotide primer ZC15132

<400> SEQUENCE: 18

```
gtaccgcgag cagttcccgt caatccctcc cccttacac aggatgtcca tattaggaca    60
tctgcgtctc gaggccaccg tggttgagcc cgacactcat tcataaaacg cttgttataa   120
aagcagtggc tgcggcgcct cgtactccaa ccgcatctgc agcgagcaac tgagaagcca   180
aggatc                                                             186
```

<210> SEQ ID NO 19
<211> LENGTH: 141
<212> TYPE: DNA
<213> ORGANISM: Artificial Sequence
<220> FEATURE:
<223> OTHER INFORMATION: 5' linker sequence

<400> SEQUENCE: 19

```
agcattgctg ctaaagaaga aggtgtaagc ttggacaaga gagaggagaa cgtggacttc    60
cgcatccacg tggagaacca gacgcgggct cgggacgatg tgagccgtaa gcagctgcgg   120
ctgtaccagc tctacagccg g                                             141
```

<210> SEQ ID NO 20
<211> LENGTH: 144
<212> TYPE: DNA
<213> ORGANISM: Artificial Sequence
<220> FEATURE:
<223> OTHER INFORMATION: 3' linker sequence

<400> SEQUENCE: 20

```
cttcagaagc ccttcaagta cacgacggtg accaagaggt cccgtcggat ccggcccaca    60
caccctgcct aggggaatt cggatcctcg agtcgacact agtattctag ggctgcctgt   120
ttggatattt ttataatttt tgag                                          144
```

<210> SEQ ID NO 21
<211> LENGTH: 243
<212> TYPE: PRT
<213> ORGANISM: Homo sapiens

<400> SEQUENCE: 21

Met Ala Ala Ala Ile Ala Ser Ser Leu Ile Arg Gln Lys Arg Gln Ala
 1               5                  10                  15

Arg Glu Ser Asn Ser Asp Arg Val Ser Ala Ser Lys Arg Arg Ser Ser
                20                  25                  30

Pro Ser Lys Asp Gly Arg Ser Leu Cys Glu Arg His Val Leu Gly Val
            35                  40                  45

Phe Ser Lys Val Arg Phe Cys Ser Gly Arg Lys Arg Pro Val Arg Arg
        50                  55                  60

Arg Pro Glu Pro Gln Leu Lys Gly Ile Val Thr Arg Leu Phe Ser Gln

```
                65                  70                  75                  80
Gln Gly Tyr Phe Leu Gln Met His Pro Asp Gly Thr Ile Asp Gly Thr
                            85                  90                  95

Lys Asp Glu Asn Ser Asp Tyr Thr Leu Phe Asn Leu Ile Pro Val Gly
                100                 105                 110

Leu Arg Val Val Ala Ile Gln Gly Val Lys Ala Ser Leu Tyr Val Ala
                115                 120                 125

Met Asn Gly Glu Gly Tyr Leu Tyr Ser Ser Asp Val Phe Thr Pro Glu
        130                 135                 140

Cys Lys Phe Lys Glu Ser Val Phe Glu Asn Tyr Tyr Val Ile Tyr Ser
145                 150                 155                 160

Ser Thr Leu Tyr Arg Gln Gln Glu Ser Gly Arg Ala Trp Phe Leu Gly
                165                 170                 175

Leu Asn Lys Glu Gly Gln Ile Met Lys Gly Asn Arg Val Lys Lys Thr
                180                 185                 190

Lys Pro Ser Ser His Phe Val Pro Lys Pro Ile Glu Val Cys Met Tyr
                195                 200                 205

Arg Glu Pro Ser Leu His Glu Ile Gly Glu Lys Gln Gly Arg Ser Arg
        210                 215                 220

Lys Ser Ser Gly Thr Pro Thr Met Asn Gly Gly Lys Val Val Asn Gln
225                 230                 235                 240

Asp Ser Thr

<210> SEQ ID NO 22
<211> LENGTH: 168
<212> TYPE: PRT
<213> ORGANISM: Homo sapiens

<400> SEQUENCE: 22

Met Ala Ser Lys Glu Pro Gln Leu Lys Gly Ile Val Thr Arg Leu Phe
1               5                   10                  15

Ser Gln Gln Gly Tyr Phe Leu Gln Met His Pro Asp Gly Thr Ile Asp
                20                  25                  30

Gly Thr Lys Asp Glu Asn Ser Asp Tyr Thr Leu Phe Asn Leu Ile Pro
            35                  40                  45

Val Gly Leu Arg Val Val Ala Ile Gln Gly Val Lys Ala Ser Leu Tyr
        50                  55                  60

Val Ala Met Asn Gly Glu Gly Tyr Leu Tyr Ser Ser Asp Val Phe Thr
65                  70                  75                  80

Pro Glu Cys Lys Phe Lys Glu Ser Val Phe Glu Asn Tyr Tyr Val Ile
                85                  90                  95

Tyr Ser Ser Thr Leu Tyr Arg Gln Gln Glu Ser Gly Arg Ala Trp Phe
                100                 105                 110

Leu Gly Leu Asn Lys Glu Gly Gln Ile Met Lys Gly Asn Arg Val Glu
            115                 120                 125

Lys Thr Lys Pro Ser Ser His Phe Val Pro Lys Pro Ile Glu Val Cys
        130                 135                 140

Met Tyr Arg Glu Pro Ser Leu His Glu Ile Gly Glu Asn Lys Gly Val
145                 150                 155                 160

Gln Gly Lys Phe Trp Thr Pro Pro
                165

<210> SEQ ID NO 23
<211> LENGTH: 247
<212> TYPE: PRT
```

<213> ORGANISM: Homo sapiens

<400> SEQUENCE: 23

```
Met Ala Ala Ile Ala Ser Gly Leu Ile Arg Gln Lys Arg Gln Ala
 1               5                  10                  15

Arg Glu Gln His Trp Asp Arg Pro Ser Ala Ser Arg Arg Ser Ser
                20                  25                  30

Pro Ser Lys Asn Arg Gly Leu Cys Asn Gly Asn Leu Val Asp Ile Phe
                35                  40                  45

Ser Lys Val Arg Ile Phe Gly Leu Lys Lys Arg Leu Arg Arg Gln
50                      55                  60

Asp Pro Gln Leu Lys Gly Ile Val Thr Arg Leu Tyr Cys Arg Gln Gly
65                      70                  75                  80

Tyr Tyr Leu Gln Met His Pro Asp Gly Ala Leu Asp Gly Thr Lys Asp
                        85                  90                  95

Asp Ser Thr Asn Ser Thr Leu Phe Asn Leu Ile Pro Val Gly Leu Arg
                100                 105                 110

Val Val Ala Ile Gln Gly Val Lys Thr Gly Leu Tyr Ile Ala Met Asn
            115                 120                 125

Gly Glu Gly Tyr Leu Tyr Pro Ser Glu Leu Phe Thr Pro Glu Cys Lys
        130                 135                 140

Phe Lys Glu Ser Val Phe Glu Asn Tyr Tyr Val Ile Tyr Ser Ser Met
145                 150                 155                 160

Leu Tyr Arg Gln Gln Glu Ser Gly Arg Ala Trp Phe Leu Gly Leu Asn
                    165                 170                 175

Lys Glu Gly Gln Ala Met Lys Gly Asn Arg Val Lys Lys Thr Lys Pro
                180                 185                 190

Ala Ala His Phe Leu Pro Lys Pro Leu Glu Val Ala Met Tyr Arg Glu
            195                 200                 205

Pro Ser Leu His Asp Val Gly Glu Thr Val Pro Lys Pro Gly Val Thr
        210                 215                 220

Pro Ser Lys Ser Thr Ser Ala Ser Ala Ile Met Asn Gly Gly Lys Pro
225                 230                 235                 240

Val Asn Lys Ser Lys Thr Thr
                245
```

<210> SEQ ID NO 24
<211> LENGTH: 245
<212> TYPE: PRT
<213> ORGANISM: Homo sapiens

<400> SEQUENCE: 24

```
Met Ala Ala Ile Ala Ser Ser Leu Ile Arg Gln Lys Arg Gln Ala
 1               5                  10                  15

Arg Glu Arg Glu Lys Ser Asn Ala Cys Lys Cys Val Ser Ser Pro Ser
                20                  25                  30

Lys Gly Lys Thr Ser Cys Asp Lys Asn Lys Leu Asn Val Phe Ser Arg
            35                  40                  45

Val Lys Leu Phe Gly Ser Lys Lys Arg Arg Arg Arg Pro Glu Pro
50                      55                  60

Gln Leu Lys Gly Ile Val Thr Lys Leu Tyr Ser Arg Gln Gly Tyr His
65                      70                  75                  80

Leu Gln Leu Gln Ala Asp Gly Thr Ile Asp Gly Thr Lys Asp Glu Asp
                        85                  90                  95

Ser Thr Tyr Thr Leu Phe Asn Leu Ile Pro Val Gly Leu Arg Val Val
```

```
                100              105              110
Ala Ile Gln Gly Val Gln Thr Lys Leu Tyr Leu Ala Met Asn Ser Glu
            115              120              125

Gly Tyr Leu Tyr Thr Ser Glu Leu Phe Thr Pro Glu Cys Lys Phe Lys
        130              135              140

Glu Ser Val Phe Glu Asn Tyr Val Thr Tyr Ser Ser Met Ile Tyr
145              150              155              160

Arg Gln Gln Gln Ser Gly Arg Gly Trp Tyr Leu Gly Leu Asn Lys Glu
                165              170              175

Gly Glu Ile Met Lys Gly Asn His Val Lys Lys Asn Lys Pro Ala Ala
            180              185              190

His Phe Leu Pro Lys Pro Leu Lys Val Ala Met Tyr Lys Glu Pro Ser
        195              200              205

Leu His Asp Leu Thr Glu Phe Ser Arg Ser Gly Ser Gly Thr Pro Thr
        210              215              220

Lys Ser Arg Ser Val Ser Gly Val Leu Asn Gly Lys Ser Met Ser
225              230              235              240

His Asn Glu Ser Thr
                245

<210> SEQ ID NO 25
<211> LENGTH: 225
<212> TYPE: PRT
<213> ORGANISM: Homo sapiens

<400> SEQUENCE: 25

Met Ala Ala Leu Ala Ser Ser Leu Ile Arg Gln Lys Arg Glu Val Arg
1               5               10              15

Glu Pro Gly Gly Ser Arg Pro Val Ser Ala Gln Arg Arg Val Cys Pro
                20              25              30

Arg Gly Thr Lys Ser Leu Cys Gln Lys Gln Leu Leu Ile Leu Leu Ser
            35              40              45

Lys Val Arg Leu Cys Gly Gly Arg Pro Ala Arg Pro Asp Arg Gly Pro
        50              55              60

Glu Pro Gln Leu Lys Gly Ile Val Thr Lys Leu Phe Cys Arg Gln Gly
65              70              75              80

Phe Tyr Leu Gln Ala Asn Pro Asp Gly Ser Ile Gln Gly Thr Pro Glu
                85              90              95

Asp Thr Ser Ser Phe Thr His Phe Asn Leu Ile Pro Val Gly Leu Arg
            100             105             110

Val Val Thr Ile Gln Ser Ala Lys Leu Gly His Tyr Met Ala Met Asn
        115             120             125

Ala Glu Gly Leu Leu Tyr Ser Ser Pro His Phe Thr Ala Glu Cys Arg
        130             135             140

Phe Lys Glu Cys Val Phe Glu Asn Tyr Tyr Val Leu Tyr Ala Ser Ala
145             150             155             160

Leu Tyr Arg Gln Arg Arg Ser Gly Arg Ala Trp Tyr Leu Gly Leu Asp
                165             170             175

Lys Glu Gly Gln Val Met Lys Gly Asn Arg Val Lys Lys Thr Lys Ala
            180             185             190

Ala Ala His Phe Leu Pro Lys Leu Leu Glu Val Ala Met Tyr Gln Glu
        195             200             205

Pro Ser Leu His Ser Val Pro Glu Ala Ser Pro Ser Ser Pro Pro Ala
        210             215             220

Pro
```

<210> SEQ ID NO 26
<211> LENGTH: 206
<212> TYPE: PRT
<213> ORGANISM: Homo sapiens

<400> SEQUENCE: 26

```
Met Ser Gly Pro Gly Thr Ala Ala Val Ala Leu Leu Pro Ala Val Leu
 1               5                  10                  15

Leu Ala Leu Leu Ala Pro Trp Ala Gly Arg Gly Gly Ala Ala Ala Pro
                20                  25                  30

Thr Ala Pro Asn Gly Thr Leu Glu Ala Glu Leu Glu Arg Arg Trp Glu
            35                  40                  45

Ser Leu Val Ala Leu Ser Leu Ala Arg Leu Pro Val Ala Ala Gln Pro
    50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
        115                 120                 125

Phe Gly Val Ala Ser Arg Phe Phe Val Ala Met Ser Ser Lys Gly Lys
    130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
        195                 200                 205
```

<210> SEQ ID NO 27
<211> LENGTH: 208
<212> TYPE: PRT
<213> ORGANISM: Homo sapiens

<400> SEQUENCE: 27

```
Met Ala Leu Gly Gln Lys Leu Phe Ile Thr Met Ser Arg Gly Ala Gly
 1               5                  10                  15

Arg Leu Gln Gly Thr Leu Trp Ala Leu Val Phe Leu Gly Ile Leu Val
                20                  25                  30

Gly Met Val Val Pro Ser Pro Ala Gly Thr Arg Ala Asn Asn Thr Leu
            35                  40                  45

Leu Asp Ser Arg Gly Trp Gly Thr Leu Leu Ser Arg Ser Arg Ala Gly
    50                  55                  60

Leu Ala Gly Glu Ile Ala Gly Val Asn Trp Glu Ser Gly Tyr Leu Val
65                  70                  75                  80

Gly Ile Lys Arg Gln Arg Arg Leu Tyr Cys Asn Val Gly Ile Gly Phe
                85                  90                  95

His Leu Gln Val Leu Pro Asp Gly Arg Ile Ser Gly Thr His Glu Glu
            100                 105                 110
```

```
Asn Pro Tyr Ser Leu Leu Glu Ile Ser Thr Val Glu Arg Gly Val Val
            115                 120                 125

Ser Leu Phe Gly Val Arg Ser Ala Leu Phe Val Ala Met Asn Ser Lys
        130                 135                 140

Gly Arg Leu Tyr Ala Thr Pro Ser Phe Gln Glu Cys Lys Phe Arg
145                 150                 155                 160

Glu Thr Leu Leu Pro Asn Asn Tyr Asn Ala Tyr Glu Ser Asp Leu Tyr
                    165                 170                 175

Gln Gly Thr Tyr Ile Ala Leu Ser Lys Tyr Gly Arg Val Lys Arg Gly
                180                 185                 190

Ser Lys Val Ser Pro Ile Met Thr Val Thr His Phe Leu Pro Arg Ile
            195                 200                 205
```

<210> SEQ ID NO 28
<211> LENGTH: 155
<212> TYPE: PRT
<213> ORGANISM: Homo sapiens

<400> SEQUENCE: 28

```
Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

<210> SEQ ID NO 29
<211> LENGTH: 155
<212> TYPE: PRT
<213> ORGANISM: Homo sapiens

<400> SEQUENCE: 29

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80
```

```
Ala Met Asp Thr Asp Gly Leu Leu Tyr Gly Ser Gln Thr Pro Asn Glu
             85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155
```

<210> SEQ ID NO 30
<211> LENGTH: 208
<212> TYPE: PRT
<213> ORGANISM: Homo sapiens

<400> SEQUENCE: 30

```
Met Trp Lys Trp Ile Leu Thr His Cys Ala Ser Ala Phe Pro His Leu
  1               5                  10                  15

Pro Gly Cys Cys Cys Cys Phe Leu Leu Phe Leu Val Ser Ser
             20                  25                  30

Val Pro Val Thr Cys Gln Ala Leu Gly Gln Asp Met Val Ser Pro Glu
             35                  40                  45

Ala Thr Asn Ser Ser Ser Ser Phe Ser Ser Pro Ser Ser Ala Gly
 50                  55                  60

Arg His Val Arg Ser Tyr Asn His Leu Gln Gly Asp Val Arg Trp Arg
 65                  70                  75                  80

Lys Leu Phe Ser Phe Thr Lys Tyr Phe Leu Lys Ile Glu Lys Asn Gly
             85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
            115                 120                 125

Asn Tyr Tyr Leu Ala Met Asn Lys Lys Gly Lys Leu Tyr Gly Ser Lys
            130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
            165                 170                 175

Tyr Val Ala Leu Asn Gly Lys Gly Ala Pro Arg Arg Gly Gln Lys Thr
            180                 185                 190

Arg Arg Lys Asn Thr Ser Ala His Phe Leu Pro Met Val Val His Ser
            195                 200                 205
```

<210> SEQ ID NO 31
<211> LENGTH: 194
<212> TYPE: PRT
<213> ORGANISM: Homo sapiens

<400> SEQUENCE: 31

```
Met His Lys Trp Ile Leu Thr Trp Ile Leu Pro Thr Leu Leu Tyr Arg
  1               5                  10                  15

Ser Cys Phe His Ile Ile Cys Leu Val Gly Thr Ile Ser Leu Ala Cys
             20                  25                  30

Asn Asp Met Thr Pro Glu Gln Met Ala Thr Asn Val Asn Cys Ser Ser
             35                  40                  45
```

```
Pro Glu Arg His Thr Arg Ser Tyr Asp Tyr Met Glu Gly Gly Asp Ile
    50                  55                  60

Arg Val Arg Arg Leu Phe Cys Arg Thr Gln Trp Tyr Leu Arg Ile Asp
 65                  70                  75                  80

Lys Arg Gly Lys Val Lys Gly Thr Gln Glu Met Lys Asn Asn Tyr Asn
                 85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
        115                 120                 125

Ala Lys Lys Glu Cys Asn Glu Asp Cys Asn Phe Lys Glu Leu Ile Leu
130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
                180                 185                 190

Ile Thr

<210> SEQ ID NO 32
<211> LENGTH: 233
<212> TYPE: PRT
<213> ORGANISM: Homo sapiens

<400> SEQUENCE: 32

Met Gly Ser Pro Arg Ser Ala Leu Ser Cys Leu Leu Leu His Leu Leu
  1               5                  10                  15

Val Leu Cys Leu Gln Ala Gln Glu Gly Pro Gly Arg Gly Pro Ala Leu
             20                  25                  30

Gly Arg Glu Leu Ala Ser Leu Phe Arg Ala Gly Arg Glu Pro Gln Gly
         35                  40                  45

Val Ser Gln Gln His Val Arg Glu Gln Ser Leu Val Thr Asp Gln Leu
    50                  55                  60

Ser Arg Arg Leu Ile Arg Thr Tyr Gln Leu Tyr Ser Arg Thr Ser Gly
 65                  70                  75                  80

Lys His Val Gln Val Leu Ala Asn Lys Arg Ile Asn Ala Met Ala Glu
                 85                  90                  95

Asp Gly Asp Pro Phe Ala Lys Leu Ile Val Glu Thr Asp Thr Phe Gly
            100                 105                 110

Ser Arg Val Arg Val Arg Gly Ala Glu Thr Gly Leu Tyr Ile Cys Met
        115                 120                 125

Asn Lys Lys Gly Lys Leu Ile Ala Lys Ser Asn Gly Lys Gly Lys Asp
130                 135                 140

Cys Val Phe Thr Glu Ile Val Leu Glu Asn Asn Tyr Thr Ala Leu Gln
145                 150                 155                 160

Asn Ala Lys Tyr Glu Gly Trp Tyr Met Ala Phe Thr Arg Lys Gly Arg
                165                 170                 175

Pro Arg Lys Gly Ser Lys Thr Arg Gln His Gln Arg Glu Val His Phe
                180                 185                 190

Met Lys Arg Leu Pro Arg Gly His His Thr Thr Glu Gln Ser Leu Arg
            195                 200                 205

Phe Glu Phe Leu Asn Tyr Pro Pro Phe Thr Arg Ser Leu Arg Gly Ser
        210                 215                 220

Gln Arg Thr Trp Ala Pro Glu Pro Arg
```

```
225                     230
```

<210> SEQ ID NO 33
<211> LENGTH: 268
<212> TYPE: PRT
<213> ORGANISM: Homo sapiens

<400> SEQUENCE: 33

```
Met Ser Leu Ser Phe Leu Leu Leu Phe Ser His Leu Ile Leu
 1               5                  10                  15

Ser Ala Trp Ala His Gly Glu Lys Arg Leu Ala Pro Lys Gly Gln Pro
                20                  25                  30

Gly Pro Ala Ala Thr Asp Arg Asn Pro Ile Gly Ser Ser Arg Gln
            35                  40                  45

Ser Ser Ser Ser Ala Met Ser Ser Ser Ala Ser Ser Pro Ala
    50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95

Ile Gly Phe His Leu Gln Ile Tyr Pro Asp Gly Lys Val Asn Gly Ser
                100                 105                 110

His Glu Ala Asn Met Leu Ser Val Leu Glu Ile Phe Ala Val Ser Gln
            115                 120                 125

Gly Ile Val Gly Ile Arg Gly Val Phe Ser Asn Lys Phe Leu Ala Met
130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
            180                 185                 190

Asn Lys Arg Gly Lys Ala Lys Arg Gly Cys Ser Pro Arg Val Lys Pro
        195                 200                 205

Gln His Ile Ser Thr His Phe Leu Pro Arg Phe Lys Gln Ser Glu Gln
    210                 215                 220

Pro Glu Leu Ser Phe Thr Val Thr Val Pro Glu Lys Lys Asn Pro Pro
225                 230                 235                 240

Ser Pro Ile Lys Ser Lys Ile Pro Leu Ser Ala Pro Arg Lys Asn Thr
                245                 250                 255

Asn Ser Val Lys Tyr Arg Leu Lys Phe Arg Phe Gly
            260                 265
```

<210> SEQ ID NO 34
<211> LENGTH: 208
<212> TYPE: PRT
<213> ORGANISM: Homo sapiens

<400> SEQUENCE: 34

```
Met Ala Pro Leu Gly Glu Val Gly Asn Tyr Phe Gly Val Gln Asp Ala
 1               5                  10                  15

Val Pro Phe Gly Asn Val Pro Val Leu Pro Val Asp Ser Pro Val Leu
                20                  25                  30

Leu Ser Asp His Leu Gly Gln Ser Glu Ala Gly Gly Leu Pro Arg Gly
            35                  40                  45

Pro Ala Val Thr Asp Leu Asp His Leu Lys Gly Ile Leu Arg Arg Arg
```

|  | 50 |  |  |  | 55 |  |  |  | 60 |  |  |  |
|---|---|---|---|---|---|---|---|---|---|---|---|---|

Gln Leu Tyr Cys Arg Thr Gly Phe His Leu Glu Ile Phe Pro Asn Gly
65                      70                    75                    80

Thr Ile Gln Gly Thr Arg Lys Asp His Ser Arg Phe Gly Ile Leu Glu
                    85                    90                    95

Phe Ile Ser Ile Ala Val Gly Leu Val Ser Ile Arg Gly Val Asp Ser
            100                  105                  110

Gly Leu Tyr Leu Gly Met Asn Glu Lys Gly Glu Leu Tyr Gly Ser Glu
          115                  120                  125

Lys Leu Thr Gln Glu Cys Val Phe Arg Glu Gln Phe Glu Glu Asn Trp
130                    135                    140

Tyr Asn Thr Tyr Ser Ser Asn Leu Tyr Lys His Val Asp Thr Gly Arg
145                    150                    155                    160

Arg Tyr Tyr Val Ala Leu Asn Lys Asp Gly Thr Pro Arg Glu Gly Thr
            165                  170                  175

Arg Thr Lys Arg His Gln Lys Phe Thr His Phe Leu Pro Arg Pro Val
            180                  185                  190

Asp Pro Asp Lys Val Pro Glu Leu Tyr Lys Asp Ile Leu Ser Gln Ser
          195                  200                  205

<210> SEQ ID NO 35
<211> LENGTH: 239
<212> TYPE: PRT
<213> ORGANISM: Homo sapiens

<400> SEQUENCE: 35

Met Gly Leu Ile Trp Leu Leu Leu Ser Leu Leu Glu Pro Gly Trp
1                5                    10                    15

Pro Ala Ala Gly Pro Gly Ala Arg Leu Arg Arg Asp Ala Gly Gly Arg
            20                  25                  30

Gly Gly Val Tyr Glu His Leu Gly Gly Ala Pro Arg Arg Arg Lys Leu
          35                  40                  45

Tyr Cys Ala Thr Lys Tyr His Leu Gln Leu His Pro Ser Gly Arg Val
50                    55                    60

Asn Gly Ser Leu Glu Asn Ser Ala Tyr Ser Ile Leu Glu Ile Thr Ala
65                    70                    75                    80

Val Glu Val Gly Ile Val Ala Ile Arg Gly Leu Phe Ser Gly Arg Tyr
            85                  90                  95

Leu Ala Met Asn Lys Arg Gly Arg Leu Tyr Ala Ser Glu His Tyr Ser
            100                  105                  110

Ala Glu Cys Glu Phe Val Glu Arg Ile His Glu Leu Gly Tyr Asn Thr
          115                  120                  125

Tyr Ala Ser Arg Leu Tyr Arg Thr Val Ser Ser Thr Pro Gly Ala Arg
130                    135                    140

Arg Gln Pro Ser Ala Glu Arg Leu Trp Tyr Val Ser Val Asn Gly Lys
145                    150                    155                    160

Gly Arg Pro Arg Arg Gly Phe Lys Thr Arg Arg Thr Gln Lys Ser Ser
            165                  170                  175

Leu Phe Leu Pro Arg Val Leu Asp His Arg Asp His Glu Met Val Arg
            180                  185                  190

Gln Leu Gln Ser Gly Leu Pro Arg Pro Gly Lys Gly Val Gln Pro
          195                  200                  205

Arg Arg Arg Arg Gln Lys Gln Ser Pro Asp Asn Leu Glu Pro Ser His
210                    215                    220

Val Gln Ala Ser Arg Leu Gly Ser Gln Leu Glu Ala Ser Ala His

```
225                 230                 235

<210> SEQ ID NO 36
<211> LENGTH: 11
<212> TYPE: PRT
<213> ORGANISM: Artificial Sequence
<220> FEATURE:
<221> NAME/KEY: VARIANT
<222> LOCATION: (1)...(11)
<223> OTHER INFORMATION: FGF family motif
<223> OTHER INFORMATION: Xaa is any amino acid

<400> SEQUENCE: 36

Cys Xaa Phe Xaa Glu Glu Glu Glu Glu Glu Tyr
1               5                   10
```